United States Patent [19]
Hillman et al.

[11] Patent Number: 5,945,287
[45] Date of Patent: Aug. 31, 1999

[54] NUCLEIC ACIDS ENCODING TWO HUMAN HEAT SHOCK PROTEIN HOMOLOGS, AND METHODS OF DETECTION THEREOF

[75] Inventors: Jennifer L. Hillman, Mountain View; Purvi Shah, Sunnyvale; Neil C. Corley, Mountain View; Preeti Lal, Santa Clara, all of Calif.

[73] Assignee: Incyte Pharmaceuticals, Inc., Palo Alto, Calif.

[21] Appl. No.: 08/974,546

[22] Filed: Nov. 19, 1997

[51] Int. Cl.$^6$ ............... C12P 21/06; C12Q 1/68; C12N 15/00; C07H 21/04
[52] U.S. Cl. ............ 435/6; 435/69.1; 435/70.1; 435/71.1; 435/91.2; 435/252.21; 435/252.3; 435/252.33; 435/320.1; 435/325; 435/348; 435/350; 435/372.2; 435/419; 536/23.1; 536/23.5; 536/24.1; 536/24.31; 536/24.33; 530/350
[58] Field of Search ................. 536/23.5, 23.1, 536/24.1, 24.31, 24.33; 530/350; 435/320.1, 325, 6, 91.2, 348, 372.2, 252.3, 252.33, 252.21, 69.1, 70.1, 71.1, 419

[56] References Cited

FOREIGN PATENT DOCUMENTS 9600300  1/1996  WIPO.

OTHER PUBLICATIONS

GenBank Accession No. T11789–published first Apr. 7, '96.

Hata, M., et al., "Genomic Cloning of a Human Heat Shock Protein 40 (Hsp40) Gene (HSPF1) and Its Chromosomal Localization to 19p13.2," *Genomics*, 38(0653):446–449 (1996) (GI 816451).

Cheret, G., et al., "DNA Sequence Analysis of the VPH1–SNF2 Region on Chromosome XV of *Saccharomyces cerevisiae*," *Genomics*, 12:1059–1064 (1996) (GI 279709).

Miron, T., et al., "A 25–kD Inhibitor of Actin Polymerization Is a Low Molecular Mass Heat Shock Protein," *The Journal of Cell Biology*, 114(2):255–261 (1991).

Marber, M., et al., "Overexpression of the Rat Inducible 70–kD Heat Stress Protein in a Transgenic Mouse Increases the Resistance of the Heart to Ischemic Injury," *J. Clin. Invest.*, 95:1446–1456 (1995).

Simon, M., et al., "Heat Shock Protein 70 Overexpression Affects the Response to Ultraviolet Light in Murine Fibroblasts," *J. Clin. Invest.*, 95:926–933 (1995).

Udono, H., and Srivastava, K., "Comparison of Tumor–Specific Immunogenicities of Stress–Induced Proteins gp96, hsp90, and hsp70[1]," *Journal of Immunology*, 152:5398–5403 (1994).

Fang, Y., et al., "Hsp90 Regulates Androgen Receptor Hormone Binding Affinity in Vivo*," *The Journal of Biological Chemistry*, 271(45):28697–28702 (1996).

Sargent, C., et al., Human major histocompatibility complex contains genes for the major heat shock protein HSP70, *Proc. Natl. Acad. Sci. USA*, 86:1968–1972 (1989).

Hendrick, J., et al., "Control of folding and membrane translocation by binding of the chaperone DnaJ to nascent polypeptides," *Proc. Natl. Acad. Sci. USA*, 90:10216–10220 (1993).

Hata, M., et al., (GI 1816451) GenBank Sequence Database (Accession D85429) National Center for Biotechnology Information, National Library of Medicine, Bethesda, Maryland 20894.

Cheret, G., et al., (GI 1279709) GenBank Sequence Database (Accession X89633) National Center for Biotechnology Information, National Library of Medicine, Bethesda, Maryland, 20894.

*Primary Examiner*—Paula K. Hutzell
*Assistant Examiner*—Geetha P. Bansal
*Attorney, Agent, or Firm*—Incyte Pharmaceuticals, Inc.

[57] ABSTRACT

The invention provides two human heat shock protein homologs (HSPHH-1, HSPHH-2) and polynucleotides which identify and encode HSPHH-1 and HSPHH-2. The invention also provides expression vectors, host cells, agonists, antibodies and antagonists. The invention also provides methods for treating disorders associated with expression of HSPHH-1 and HSPHH-2.

10 Claims, 10 Drawing Sheets

FIGURE 1A

```
                        9            18           27           36           45           54
5'   GG  ACG  GAG  CCG  GGG  GAG  GCA  GCG  GCT  GTC  TCA  CGG  ACC  ACG  GCG  GCG  CCC 63           72           81           90           99           108
     GCA  GCT  CCT  CAC  CGA  AAC  AAG  GAG  ACC  AGT  GCT  GTG  CCA  GTG  GCT  GTG  ATG  GGA
                                                                                     M    G 117          126          135          144          153          162
     AAA  GAT  TAT  AAG  ATT  CTT  GGG  ATC  CCA  TCG  GGG  GCC  AAC  GAG  GAT  GAG  ATC
      K    D    Y    K    I    L    G    I    P    S    G    A    N    E    D    E    I 171          180          189          198          207          216
     AAG  GCC  TAC  CGG  AAG  ATG  GCC  TTG  AAG  TAC  CAC  CCA  GAC  AAG  AAT  AAA  GAA
      K    A    Y    R    K    M    A    L    K    Y    H    P    D    K    N    K    E 225          234          243          252          261          270
     CCC  AAC  GCT  GAG  GAG  AAG  TTT  AAG  GAG  ATT  GCA  GAG  GCC  TAT  GAT  GTG  CTA  AGT
      P    N    A    E    E    K    F    K    E    I    A    E    A    Y    D    V    L    S 279          288          297          306          315          324
     GAC  CCC  AAG  AAA  CGG  GGC  CTG  TAT  GAC  CAG  TAT  GGG  GAG  GAA  GGC  CTG  AAG  ACC
      D    P    K    K    R    G    L    Y    D    Q    Y    G    E    E    G    L    K    T 333          342          351          360          369          378
     GGC  GGT  ACA  TCA  GGT  TCC  AGT  GGC  TCC  TTT  CAC  TAC  TAC  TTT  CAT  GGG
      G    G    T    S    G    S    S    G    S    F    H    Y    Y    F    H    G
```

```
      387         396         405         414         423         432
GAC CCC CAT GCC ACC TTT GCC TCC TTC TTT GGT GGC TCC AAC CCC TTC GAT ATC
 D   P   H   A   T   F   A   S   F   F   G   G   S   N   P   F   D   I 441                     450         459         468         477         486
TTC TTT GCC AGC AGC CGC TCC ACT CGG CCC TTC AGT GGC CCA GAT GAC
 F   F   A   S   S   R   S   T   R   P   F   S   G   P   D   D 495         504         513         522         531         540
ATG GTG GAT GAA GAT GAG GAC CCA TTT GGC GCT TTC GGC CGT TTT GGC TTC
 M   V   D   E   D   E   D   P   F   G   A   F   G   R   F   G   F 549         558         567         576         585         594
AAT GGG CTG AGT AGG GGT CCA AGG CGA GCC CCA GAA CCA CTG TAC CCT CGG CGC
 N   G   L   S   R   G   P   R   R   A   P   E   P   L   Y   P   R   R 603         612         621         630         639         648
AAG GTG CAG GAC CCC AAG ATG CCA GTG GTG CGG GTG TCC CTG GAG GAG ATC
 K   V   Q   D   P   K   M   P   V   V   R   V   S   L   E   E   I 657                     666         675         684         693         702
TAC CAT GGC TCC ACC AAG GAC AAG ATC ACA AAG ATC CGC CTC AAC CCT GAT
 Y   H   G   S   T   K   D   K   I   T   K   I   R   R   L   N   P   D 711         720         729         738         747         756
GGG CGA ACT GTG CGC ACC GAG GAC AAG ATC CTG CAC ATA GTC ATC AAG CGT GGC
 G   R   T   V   R   T   E   D   K   I   L   H   I   V   I   K   R   G
```

```
     765              774         783         792         801         810
TGG AAG GAA GGC ACC AAG ATC ACC TTC CCC AAA GAA GGC GAC GCC ACA CCT GAC
 W   K   E   G   T   K   I   T   F   P   K   E   G   D   A   T   P   D 819              828         837         846         855         864
AAC ATC CCT GCT GAC ATC GTC TTT GTG CTC AAA GAC AAG CCC CAT GCA CAC TTC
 N   I   P   A   D   I   V   F   V   L   K   D   K   P   H   A   H   F 873              882         891         900         909         918
CGC CGA GAT GGC ACC AAC GTG CTC TAC AGT GCC CTG ATC AGC AAG GAG GCG
 R   R   D   G   T   N   V   L   Y   S   A   L   I   S   K   E   A 927              936         945         954         963         972
CTG TGT GGC TGC ACT GTG AAC ATT CCC ACT ATC GAC GGC CGA GTG ATC CCT TTG
 L   C   G   C   T   V   N   I   P   T   I   D   G   R   V   I   P   L 981              990         999         1008        1017        1026
CCC TGC AAT GAT GTC ATC AAG CCA ACT CAG GGC ACC GTG AAG AGA CTC CGT GGG GAG GGC
 P   C   N   D   V   I   K   P   T   Q   G   T   V   K   R   L   R   G   E   G 1035             1044        1053        1062        1071        1080
CTT CCC TTC CCC AAA GTG CCA ACT CAG CGA GGA GAC CTC ATT GTT GAG TTC AAA
 L   P   F   P   K   V   P   T   Q   R   G   D   L   I   V   E   F   K 1089             1098        1107        1116        1125        1134
GTT CGC TTC CCA GAC AGA TTA ACA CCA CAG ACA AGA CAG ATC CTT AAG CAG CAC
 V   R   F   P   D   R   L   T   P   Q   T   R   Q   I   L   K   Q   H
```

```
            1143           1152           1161           1170           1179           1188
      CTA CCC TGT TCC TAG GCT CTG CCC CAG CCA GTC CAG AGC CTA CCA CAG CAA TAC
       L   P   C   S 1197           1206           1215           1224           1233           1242
      CCC CAA CAC TCA CTC CAC TCA ATG TGC ACC CAG CTT GAT GTC CAC TGG ACA CTG 1251           1260           1269           1278           1287           1296
      GCA ACT TTT TCT AAA ATG CAA AAA AAA GCC ACT GGT TTT CAG GAA AAT GTT CCT 1305           1314           1323           1332           1341           1350
      GTC CCT GAC CCC TTT TAG AGC TGG GCT GCC TGG GGG GAG TTG GAG GGA GGT GGG 1359           1368           1377           1386           1395           1404
      GAG AGC TAG CCC AGG CCA GGG GTC AAT GTT CAT GTC ACT AGC TTT CAA TCC A 1413           1422           1431           1440           1449           1458
      TTC CAC TGC AGT GGC TGG AGA GTG ACC TGA GTG CTA CTT GAA GAT ATG TAG AGA 1467           1476           1485           1494           1503           1512
      TTC CTT ATC CAT GCC TGT ACA TAG CAT GTC CTC CTC CCC TCA GCT TTG CTA ATA 1521           1530           1539           1548           1557           1566
      CCA GTC CCC TCC CTT CCC TTT GGC TTC CTG CTG TTG GGG GTG GAA AAG ACT AGA 1575           1584           1593           1602           1611           1620
      AAG GAC ATT GCT TTC TCA GCC CCA CCC CCA GGT CCA CAG TGT CCA AGG TAA TGG

FIGURE 1D
```

```
     1629       1638       1647       1656       1665       1674
CAC ACA TAT TCA TGC ACA AGA AGC ACT CAC CTA GAG CTG TCT GTG CCT CTC TGG
     1683       1692       1701       1710       1719       1728
GAG AAA GGA GAG AGG ATA AGA AGG GAA AGT TCA CAA CCT GTG AAC AGG GAC TTG
     1737       1746       1755       1764       1773       1782
AGC ACG AGA CAC TTT TCA TCT GGA GCA GGG GGG TGA GCT CCT CAG CAG CCT CCG
     1791       1800       1809       1818       1827       1836
TAA CAG CTG CCC CTA CAC CTG CAG AGC TGG AGG TTC TGT CCT CCC TGC TGC
     1845       1854       1863       1872       1881       1890
TCT CAG GAG TGT TCA AGG GTG GAG GGC AGG GAA TGG GGC CTG AGG TAT TAA GGC
     1899       1908       1917       1926       1935       1944
TAA GAG GTG GGG GAC AGG GCC CAT CTA CCA GCC TTC ATC AGG AAG GGA AAG GGC
     1953       1962       1971       1980       1989       1998
TTT GGG GTC AGG TGG CAG CTA TTC CCC ACC AAG AGA TTC AGG GTC ACA GGT TTT
     2007       2016       2025       2034       2043       2052
TCC CCA CAC CTC TGA ACT CAG GGC CTA GCC ACC CCC AAA CTT CCA AAT CCC ACT
     2061       2070       2079       2088       2097       2106
TTT GTG ATA TGT GAA GCT ACT CAT TTC TTA CCC TTG GAG GCT GTG TGG GGA ATT
```

FIGURE 1E

```
                2115            2124            2133            2142            2151            2160
TCC AGC CCT TTT ATG CCT GTG TGA TCC CAC CCC ACC CCC ATA GTT GTA TAA AGG
      2169            2178            2187            2196            2205            2214
TCA TAG TGA AGA AGC TGG GGG AAG ACT GCT TCA GCC AGA TCC TGG GGT GGG GTC
      2223            2232            2241            2250            2259            2268
TTT AGG TTT TCT CAC TTT GAC AAC CCC CGA ATG TTT TTA TAG TAG TTT TTT TGT
      2277            2286            2295            2304            2313            2322
ATT TTT TTG TAA TGA CAG TAT TAT GTA AAA AAT AAA GTA TTT TAA AAA TAN AAA
      2331            2340            2349
AAA ATG TTC AAA TCA CAA GTG TCA TGA T 3'
```

FIGURE 1F

```
1    MGKDYYKILGIPSGANEDEIKKAYRKMALKYHPDKNKEPN      2525691
1    MGKDYYQTLGLARGASDEEIKRAYRRQALRYHPDKNKEPG      GI 1816452

41   AEEKFKEIAEAYDVLSDPKKRGLYDQYGEEGLK---TGG       2525691
41   AEEKFKEIAEAYDVLSDPRKREIFDRYGEEGLKGSGPSGG      GI 1816452

77   GTSGGSSGSFHYTFHGDPHATFASFFGGSNPFDIFFASSR      2525691
81   SGGGANGTSFSYTFHGDPHAMFAEFFGGRNPFDTFFGQRN      GI 1816452

117  STRPFSGFDPDDMDVDEDEDPFGAF--GRFGFNGLSRGPR      2525691
121  GE--------EGMDID---DPFSGFPMGMGGFTNVNFGRS      GI 1816452

155  RAPEPLYPRRKVQDPPVVHELRVSLEEIYHGSTKRMKITR      2525691
150  RSAQE--PARKKQDPPVTHDLRVSLEEIYSGCTKKMKISH      GI 1816452

195  RRLNPDGRTVRTEDKILHIVIKRGWKEGTKITFPKEGDAT      2525691
188  KRLNPDGKSIRNEDKILTIEVKKGWKEGTKITFPKEGDQT      GI 1816452

235  PDNIPADIVFVLKDKPHAHFRRDGTNVLYSALISLKEALC      2525691
228  SNNIPADIVFVLKDKPHNIFKRDGSDVIYPARISLREALC      GI 1816452

275  GCTVNIPTIDGRVIPLPCNDVIKPGTVKRLRGEGLPFPKV      2525691
268  GCTVNVPTLDGRTIPVVFKDVIRPGMRRKVPGEGLPLPKT      GI 1816452

315  PTQRGDLIVEFKVRFPDRLTPQTRQILKQHLPCS           2525691
308  PEKRGDLIEFEVIFPERIPQTSRTVLEQVLP-I            GI 1816452
```

FIGURE 2

```
                                                                        54
5' NNT TCC GGA TCC CTC AGC TCT AGG AGG GAA CGG GAG ATG TTG CAG GCG CCG
                                                          M   L   Q   A   P

108
   AGA GGG CGG GCC AGG GCC GCA CTC CGG AGA CTC GCG GTT GCT ACG CGC ATG
   R   G   R   A   R   A   A   L   R   R   L   A   V   A   T   R   M

162
   GCT GGA GCG CCC ACG GTC TCG CTT CCT GAA CTC CGT TCA CTC GCC TCC GGA
   A   G   A   P   T   V   S   L   P   E   L   R   S   L   A   S   G

216
   CGG GCC CGG CTC TTC GAC GTG CGC GAG TCT CGC GAG GAG GCG GCA GCT ACC ATC
   R   A   R   L   F   D   V   R   E   S   R   E   E   A   A   A   T   I

270
   CCA GGG GCG CTC AAC ATC CCG GTG TCC GAG TTG GAG AGT GCT GGG ACC GAG
   P   G   A   L   N   I   P   V   S   E   L   E   S   A   G   T   E

324
   CCA GCT GCC TTC CAG GCT TTA TAT TCT GCT GAG AAG CCA AAG CTG CAG ATG GAG
   P   A   A   F   Q   A   L   Y   S   A   E   K   P   K   L   Q   M   E

378
   CCA GGG GTT TTC TGT CAG ATG GGC AAG CGG GGC CTC CAG ACG CAG GAT GAG
   P   G   V   F   C   Q   M   G   K   R   G   L   Q   T   Q   D   E

CAT CTC GTT TTC TTC TGT CAG ATG GGC AAG CGG GGC CTC CAG ACG CAG CTG
   H   L   V   F   F   C   Q   M   G   K   R   G   L   Q   T   Q   L
```

FIGURE 3A

```
           387      396      405      414      423      432
    GCC CGG AGT CTT GGA TAC ACT GGG GCT CGC AAC TAC GCT GGA GCC TAT AGA GAA
     A   R   S   L   G   Y   T   G   A   R   N   Y   A   G   A   Y   R   E 441      450      459      468      477      486
    TGG TTG GAG AAA GAG AGT TAG GCA GGA GGC AGC TTA CTG ATT GCC ACC CCC TGG
     W   L   E   K   E   S 495      504      513      522      531      540
    CCC CTT AAT GGC CAC CTT AAC TAA GGG TGT GAA CGG GCT GAC TTG GTG AAT TGG 549      558      567      576      585      594
    GCA ACT CCT TAT AGT GTT GTG CAC ACA AAA GCA TCA AAT AAA GAA CAT TTA ATC

NUCLEIC ACIDS ENCODING TWO HUMAN HEAT SHOCK PROTEIN HOMOLOGS, AND METHODS OF DETECTION THEREOF

FIELD OF THE INVENTION

This invention relates to nucleic acid and amino acid sequences of two human heat shock protein homologs and to the use of these sequences in the diagnosis, prevention, and treatment of cancer and inflammation.

BACKGROUND OF THE INVENTION

Induction of heat shock proteins (Hsps), a class of molecular chaperones, is a physiological and biochemical response to abrupt increases in temperature or exposure to a variety of other metabolic insults including heavy metals, amino acid analogs, toxins, and oxidative stress. This response occurs in all prokaryotic and eukaryotic cells and is characterized by repression of normal protein synthesis and initiation of transcription of Hsp-encoding genes. Under normal or nonstressed conditions, constitutively expressed Hsps facilitate proper protein folding and maturation, promote protein translocation across membranes, and regulate hormone receptor and protein kinase activity.

Hsps function by associating with cellular proteins and regulating their conformation. The conformational properties of a protein determine protein activity, aggregation, degradation, and function. Hsp70s act by maintaining proteins in an unfolded conformation, while Hsp60/GroEL complexes act by facilitating protein folding. Hsp90s act in a maturational or regulatory capacity on specific molecules including steroid hormone receptors. The small Hsps are able to suppress aggregation and heat inactivation of various proteins, including actin. Hsp40, the mammalian homolog of bacterial DnaJ heat shock protein, binds to new polypeptide chains as they are being synthesized on ribosomes and mediates their correct folding. A cluster of seven small Hsp genes has been identified in Saccharomyces cerevisiae which have sequence and organizational similarities to the seven heat shock genes in Drosophila melanogaster chromosomal locus 67B. These seven genes are coordinately expressed following heat shock. In contrast to their uniform induction by heat shock, these genes are differentially expressed during several developmental stages (Hata, M. et al. (1996) Genomics 38:446–449; Cheret, G. et al. (1996) Genomics 12:1059–1064; and Miron, T. et al. (1991) J. Cell Biol. 114: 255–261).

Overexpression of Hsps in transgenic mice and rats or prior heat treatment of normal animals to induce Hsps protects the heart muscle from ischemic injury. Both heat shock-induced and exogenous Hsps protect smooth muscle cells from serum deprivation-induced cell death. Overexpression of Hsps also protects murine fibroblasts from both UV light injury and proinflammatory cytokines released during UV exposure. (Marber, M. S. et al. (1995) J. Clin. Invest. 95: 1446–1456; Simon, M. M. et al. (1995) J. Clin. Invest. 95: 926–933).

Hsps are located in all major cellular compartments and function as monomers, multimers, or complexed with other cellular proteins. Hsps bind to steroid hormone receptors, repress transcription in the absence of the ligand, and provide the proper folding of the ligand-binding domain in the presence of the hormone. Specific Hsps bind immunosuppressive drugs and may play a role in modulation of immune responses. Hsps expressed in cancer cells can protect the cancer cells from the cytotoxic effects of drugs used in anticancer therapies. Hsps isolated from tumor cells, when purified and used as an antigen, have been shown to provide immunity to the tumors from which they are isolated (Udono, H. et al. (1994) J. Immunol. 152: 5398–5403; Fang, Y. et al. (1996) J. Biol. Chem. 271: 28697–28702).

Several of the constitutive Hsp genes are located in the major histocompatibility complex on chromosome 6, and members of the Hsp family play roles in T-cell mediated regulation of inflammation and immune recognition. Heat shock treatment of B-cells enhances processing of antigen and the assembly and function of MHC class II molecules (Sargent, C. A. et al. (1989) Proc. Natl. Acad. Sci. 86; 1968–1972; Hendrick, J. P. et al. (1993) Proc. Natl. Acad. Sci. 90: 10216–10220).

The discovery of two human heat shock protein homologs and the polynucleotides encoding them satisfies a need in the art by providing new compositions which are useful in the diagnosis, prevention and treatment of cancer and inflammation.

SUMMARY OF THE INVENTION

The invention features substantially purified polypeptides, two human heat shock protein homologs, referred to collectively as "HSPHH" and individually as "HSPHH-1" and "HSPHH-2." In one aspect, the invention provides a substantially purified polypeptide, HSPHH, comprising an amino acid sequence selected from the group consisting of SEQ ID NO:1, SEQ ID NO:3, a fragment of SEQ ID NO:1, and a fragment of SEQ ID NO:3.

The invention further provides a substantially purified variant of HSPHH having at least 90% amino acid identity to the amino acid sequences of SEQ ID NO:1 or SEQ ID NO:3, or to a fragment of either SEQ ID NO:1 or SEQ ID NO:3. The invention also provides an isolated and purified polynucleotide sequence encoding SEQ ID NO:1, SEQ ID NO:3, a fragment of SEQ ID NO:1, and a fragment of SEQ ID NO:3. The invention also provides an isolated and purified polynucleotide variant having at least 90% polynucleotide identity to the polynucleotide sequence encoding the polypeptide comprising an amino acid sequence selected from the group consisting of SEQ ID NO:1, SEQ ID NO:3, a fragment of SEQ ID NO:1, and a fragment of SEQ ID NO:3.

Additionally, the invention provides a composition comprising a polynucleotide sequence encoding the polypeptide comprising the amino acid sequence selected from the group consisting of SEQ ID NO:1, SEQ ID NO:3, a fragment of SEQ ID NO:1, and a fragment of SEQ ID NO:3. The invention further provides an isolated and purified polynucleotide sequence which hybridizes under stringent conditions to the polynucleotide sequence encoding the polypeptide comprising an amino acid sequence selected from the group consisting of SEQ ID NO:1, SEQ ID NO:3, a fragment of SEQ ID NO:1, and a fragment of SEQ ID NO:3, as well as an isolated and purified polynucleotide sequence which is complementary to the polynucleotide sequence encoding the polypeptide comprising an amino acid sequence selected from the group consisting of SEQ ID NO:1, SEQ ID NO:3, a fragment of SEQ ID NO:1, and a fragment of SEQ ID NO:3

The invention also provides an isolated and purified polynucleotide sequence comprising a polynucleotide sequence selected from the group consisting of SEQ ID NO:2, SEQ ID NO:4, a fragment of SEQ ID NO:2, and a fragment of SEQ ID NO:4. The invention further provides an isolated and purified polynucleotide variant having at least 90% polynucleotide identity to the polynucleotide sequence comprising a polynucleotide sequence selected from the group consisting of SEQ ID NO:2, SEQ ID NO:4, a fragment of SEQ ID NO:2, and a fragment of SEQ ID NO:4, as well as an isolated and purified polynucleotide sequence which is complementary to the polynucleotide sequence comprising a polynucleotide sequence selected from the group consisting of SEQ ID NO:2, SEQ ID NO:4, a fragment of SEQ ID NO:2, and a fragment of SEQ ID NO:4.

The invention further provides an expression vector containing at least a fragment of the polynucleotide sequence encoding the polypeptide comprising an amino acid sequence selected from the group consisting of SEQ ID NO:1 or SEQ ID NO:3, a fragment of SEQ ID NO:1, and a fragment of SEQ ID NO:3. In another aspect, the expression vector is contained within a host cell.

The invention also provides a method for producing a polypeptide comprising the amino acid sequence of SEQ ID NO:1, SEQ ID NO:3, a fragment of SEQ ID NO:1, and a fragment of SEQ ID NO:3, the method comprising the steps of: (a) culturing the host cell containing an expression vector containing at least a fragment of a polynucleotide sequence encoding HSPHH under conditions suitable for the expression of the polypeptide; and (b) recovering the polypeptide from the host cell culture.

The invention also provides a pharmaceutical composition comprising a substantially purified HSPHH having the amino acid sequence of SEQ ID NO:1, SEQ ID NO:3, a fragment of SEQ ID NO:1, or a fragment of SEQ ID NO:3 in conjunction with a suitable pharmaceutical carrier.

The invention further includes a purified antibody which binds to the amino acid sequence of SEQ ID NO:1, SEQ ID NO:3, a fragment of SEQ ID NO:1, or a fragment of SEQ ID NO:3, (HSPHH) as well as a purified agonist and a purified antagonist to the sequence of SEQ ID NO:1, SEQ ID NO:3, a fragment of SEQ ID NO:1, or a fragment of SEQ ID NO:3, (HSPHH).

The invention also provides a method for treating or preventing a cancer, the method comprising administering to a subject in need of such treatment an effective amount of an antagonist of HSPHH The invention also provides a method for treating or preventing inflammation, the method comprising administering to a subject in need of such treatment an effective amount of an antagonist of HSPHH The invention also provides a method for detecting a polynucleotide encoding HSPHH in a biological sample containing nucleic acid material, the method comprising the steps of: (a) hybridizing the complement of the polynucleotide sequence which encodes the polypeptide comprising SEQ ID NO:1, SEQ ID NO:3, a fragment of SEQ ID NO:1, or a fragment of SEQ ID NO:3 to the nucleic acid material of the biological sample, thereby forming a hybridization complex; and (b) detecting the hybridization complex, wherein the presence of the hybridization complex correlates with the presence of a polynucleotide encoding HSPHH in the biological sample. In one aspect, the nucleic acid material of the biological sample is amplified by the polymerase chain reaction prior to the hybridizing step.

BRIEF DESCRIPTION OF THE FIGURES

FIGS. 1A, 1B, 1C, 1D, 1E, and 1F show the amino acid sequence (SEQ ID NO:1) and nucleic acid sequence (SEQ ID NO:2) of HSPHH-1. The alignment was produced using MacDNASIS PRO™ software (Hitachi Software Engineering Co. Ltd. San Bruno, Calif.).

FIG. 2 shows the amino acid sequence alignments between HSPHH-1 (2525691; SEQ ID NO:1) and human Hsp40 (GI 1816452; SEQ ID NO:5), produced using the multisequence alignment program of DNASTAR™ software (DNASTAR Inc, Madison Wis.).

FIGS. 3A and 3B show the amino acid sequence (SEQ ID NO:3) and nucleic acid sequence (SEQ ID NO:4) of HSPHH-2. The alignment was produced using MacDNASIS PRO™ software (Hitachi Software Engineering Co. Ltd. San Bruno, Calif.).

FIG. 4 shows the amino acid sequence alignments between HSPHH-2 (3172266; SEQ ID NO:3) and *Saccharomyces cerevisiae* heat shock protein (GI 1279709; SEQ ID NO:6), produced using the multisequence alignment program of DNASTAR™ software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a host cell" includes a plurality of such host cells, reference to the "antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are incorporated herein by reference for the purpose of describing and disclosing the cell lines, vectors, and methodologies which are reported in the publications which might be used in connection with the invention. Nothing herein is to be construed as an admission that the invention is not entitled to antedate such disclosure by virtue of prior invention.

Definitions

HSPHH, as used herein, refers to the amino acid sequences of substantially purified HSPHH obtained from any species, particularly mammalian, including bovine, ovine, porcine, murine, equine, and preferably human, from any source whether natural, synthetic, semi-synthetic, or recombinant.

The term "agonist", as used herein, refers to a molecule which, when bound to HSPHH, increases or prolongs the duration of the effect of HSPHH. Agonists may include proteins, nucleic acids, carbohydrates, or any other molecules which bind to and modulate the effect of HSPHH.

An "allele" or "allelic sequence", as used herein, is an alternative form of the gene encoding HSPHH. Alleles may result from at least one mutation in the nucleic acid sequence and may result in altered mRNAs or polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HSPHH as used herein include those with deletions, insertions, or substitutions of different nucleotides resulting in a polynucleotide that encodes the same or a functionally equivalent HSPHH. Included within this definition are polymorphisms which may or may not be readily detectable using a particular oligonucleotide probe of the polynucleotide encoding HSPHH, and improper or unexpected hybridization to alleles, with a locus other than the normal chromosomal locus for the polynucleotide sequence encoding HSPHH. The encoded protein may also be "altered" and contain deletions, insertions, or substitutions of amino acid residues which produce a silent change and result in a functionally equivalent HSPHH. Deliberate amino acid substitutions may be made on the basis of similarity in polarity, charge, solubility, hydrophobicity, hydrophilicity, and/or the amphipathic nature of the residues as long as the biological or immunological activity of HSPHH is retained. For example, negatively charged amino acids may include aspartic acid and glutamic acid; positively charged amino acids may include lysine and arginine; and amino acids with uncharged polar head groups having similar hydrophilicity values may include leucine, isoleucine, and valine, glycine and alanine, asparagine and glutamine, serine and threonine, and phenylalanine and tyrosine.

"Amino acid sequence" as used herein refers to an oligopeptide, peptide, polypeptide, or protein sequence, and fragment thereof, and to naturally occurring or synthetic molecules. Fragments of HSPHH are preferably about 5 to about 15 amino acids in length and retain the biological activity or the immunological activity of HSPHH. Where "amino acid sequence" is recited herein to refer to an amino acid sequence of a naturally occurring protein molecule, amino acid sequence, and like terms, are not meant to limit the amino acid sequence to the complete, native amino acid sequence associated with the recited protein molecule.

"Amplification" as used herein refers to the production of additional copies of a nucleic acid sequence and is generally carried out using polymerase chain reaction (PCR) technologies well known in the art (Dieffenbach, C. W. and G. S. Dveksler (1995) *PCR Primer, a Laboratory Manual,* Cold Spring Harbor Press, Plainview, N.Y.).

The term "antagonist" as used herein, refers to a molecule which, when bound to HSPHH, decreases the amount or the duration of the effect of the biological or immunological activity of HSPHH. Antagonists may include proteins, nucleic acids, carbohydrates, antibodies or any other molecules which decrease the effect of HSPHH.

As used herein, the term "antibody" refers to intact molecules as well as fragments thereof, such as Fa, F(ab')$_2$, and Fv, which are capable of binding the epitopic determinant. Antibodies that bind HSPHH polypeptides can be prepared using intact polypeptides or fragments containing small peptides of interest as the immunizing antigen. The polypeptide or oligopeptide used to immunize an animal can be derived from the translation of RNA or synthesized chemically and can be conjugated to a carrier protein, if desired. Commonly used carriers that are chemically coupled to peptides include bovine serum albumin and thyroglobulin, keyhole limpet hemocyanin. The coupled peptide is then used to immunize the animal (e.g., a mouse, a rat, or a rabbit).

The term "antigenic determinant", as used herein, refers to that fragment of a molecule (i.e., an epitope) that makes contact with a particular antibody. When a protein or fragment of a protein is used to immunize a host animal, numerous regions of the protein may induce the production of antibodies which bind specifically to a given region or three-dimensional structure on the protein; these regions or structures are referred to as antigenic determinants. An antigenic determinant may compete with the intact antigen (i.e., the immunogen used to elicit the immune response) for binding to an antibody.

The term "antisense", as used herein, refers to any composition containing nucleotide sequences which are complementary to a specific DNA or RNA sequence. The term "antisense strand" is used in reference to a nucleic acid strand that is complementary to the "sense" strand. Antisense molecules include peptide nucleic acids and may be produced by any method including synthesis or transcription. Once introduced into a cell, the complementary nucleotides combine with natural sequences produced by the cell to form duplexes and block either transcription or translation. The designation "negative" is sometimes used in reference to the antisense strand, and "positive" is sometimes used in reference to the sense strand.

The term "biologically active", as used herein, refers to a protein having structural, regulatory, or biochemical functions of a naturally occurring molecule. Likewise, "immunologically active" refers to the capability of the natural, recombinant, or synthetic HSPHH, or any oligopeptide thereof, to induce a specific immune response in appropriate animals or cells and to bind with specific antibodies.

The terms "complementary" or "complementarity", as used herein, refer to the natural binding of polynucleotides under permissive salt and temperature conditions by base-pairing. For example, the sequence "A-G-T" binds to the complementary sequence "T-C-A". Complementarity between two single-stranded molecules may be "partial", in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acids strands and in the design and use of PNA molecules.

A "composition comprising a given polynucleotide sequence" as used herein refers broadly to any composition containing the given polynucleotide sequence. The composition may comprise a dry formulation or an aqueous solution. Compositions comprising polynucleotide sequences encoding HSPHH or fragments thereof (e.g., SEQ ID NO:2 and SEQ ID NO:4 and fragments thereof) may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS) and other components (e.g., Denhardt's solution, dry milk, salmon sperm DNA, etc.).

"Consensus", as used herein, refers to a nucleic acid sequence which has been resequenced to resolve uncalled bases, has been extended using XL-PCR™ (Perkin Elmer, Norwalk, Conn.) in the 5' and/or the 3' direction and resequenced, or has been assembled from the overlapping sequences of more than one Incyte Clone using a computer program for fragment assembly (e.g., GELVIEW™ Fragment Assembly system, GCG, Madison, Wis.). Some sequences have been both extended and assembled to produce the consensus sequence.

The term "correlates with expression of a polynucleotide", as used herein, indicates that the detection of the presence of ribonucleic acid that is similar to SEQ ID:NO:2 and SEQ ID NO:4 by northern analysis is indicative of the presence of mRNA encoding HSPHH in a sample and thereby correlates with expression of the transcript from the polynucleotide encoding the protein.

A "deletion", as used herein, refers to a change in the amino acid or nucleotide sequence and results in the absence of one or more amino acid residues or nucleotides.

The term "derivative", as used herein, refers to the chemical modification of a nucleic acid encoding or complementary to HSPHH or the encoded HSPHH. Such modifications include, for example, replacement of hydrogen by an alkyl, acyl, or amino group. A nucleic acid derivative encodes a polypeptide which retains the biological or immunological function of the natural molecule. A derivative polypeptide is one which is modified by glycosylation, pegylation, or any similar process which retains the biological or immunological function of the polypeptide from which it was derived.

The term "homology", as used herein, refers to a degree of complementarity. There may be partial homology or complete homology (i.e., identity). A partially complementary sequence that at least partially inhibits an identical sequence from hybridizing to a target nucleic acid is referred to using the functional term "substantially homologous." The inhibition of hybridization of the completely complementary sequence to the target sequence may be examined using a hybridization assay (Southern or northern blot, solution hybridization and the like) under conditions of low stringency. A substantially homologous sequence or hybridization probe will compete for and inhibit the binding of a completely homologous sequence to the target sequence under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target sequence which lacks even a partial degree of complementarity (e.g., less than about 30% identity). In the absence of non-specific binding, the probe will not hybridize to the second non-complementary target to the second non-complementary target sequence.

Human artificial chromosomes (HACs) are linear microchromosomes which may contain DNA sequences of 10K to 10M in size and contain all of the elements required for stable mitotic chromosome segregation and maintenance (Harrington, J. J. et al. (1997) Nat Genet. 15: 345–355).

The term "humanized antibody", as used herein, refers to antibody molecules in which amino acids have been replaced in the non-antigen binding regions in order to more closely resemble a human antibody, while still retaining the original binding ability.

The term "hybridization", as used herein, refers to any process by which a strand of nucleic acid binds with a complementary strand through base pairing.

The term "hybridization complex", as used herein, refers to a complex formed between two nucleic acid sequences by virtue of the formation of hydrogen bonds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

An "insertion" or "addition", as used herein, refers to a change in an amino acid or nucleotide sequence resulting in the addition of one or more amino acid residues or nucleotides, respectively, as compared to the naturally occurring molecule.

"Microarray" refers to an array of distinct polynucleotides or oligonucleotides synthesized on a substrate, such as paper, nylon or other type of membrane, filter, chip, glass slide, or any other suitable solid support.

The term "modulate", as used herein, refers to a change in the activity of HSPHH. For example, modulation may cause an increase or a decrease in protein activity, binding characteristics, or any other biological, functional or immunological properties of HSPHH.

"Nucleic acid sequence" as used herein refers to an oligonucleotide, nucleotide, or polynucleotide, and fragments thereof, and to DNA or RNA of genomic or synthetic origin which may be single- or double-stranded, and represent the sense or antisense strand. "Fragments" are those nucleic acid sequences which are greater than 60 nucleotides than in length, and most preferably includes fragments that are at least 100 nucleotides or at least 1000 nucleotides, and at least 10,000 nucleotides in length.

The term "oligonucleotide" refers to a nucleic acid sequence of at least about 6 nucleotides to about 60 nucleotides, preferably about 15 to 30 nucleotides, and more preferably about 20 to 25 nucleotides, which can be used in PCR amplification or a hybridization assay, or a microarray. As used herein, oligonucleotide is substantially equivalent to the terms "amplimers", "primers", "oligomers", and "probes", as commonly defined in the art.

"Peptide nucleic acid", PNA as used herein, refers to an antisense molecule or anti-gene agent which comprises an oligonucleotide of at least five nucleotides in length linked to a peptide backbone of amino acid residues which ends in lysine. The terminal lysine confers solubility to the composition. PNAs may be pegylated to extend their lifespan in the cell where they preferentially bind complementary single stranded DNA and RNA and stop transcript elongation (Nielsen, P. E. et al. (1993) Anticancer Drug Des. 8: 53–63).

The term "portion", as used herein, with regard to a protein (as in "a portion of a given protein") refers to fragments of that protein. The fragments may range in size from five amino acid residues to the entire amino acid sequence minus one amino acid. Thus, a protein "comprising at least a portion of the amino acid sequence of HSPHH" encompasses the full-length HSPHH and fragments thereof.

The term "sample", as used herein, is used in its broadest sense. A biological sample suspected of containing nucleic acid encoding HSPHH, or fragments thereof, or HSPHH itself may comprise a bodily fluid, extract from a cell, chromosome, organelle, or membrane isolated from a cell, a cell, genomic DNA, RNA, or cDNA (in solution or bound to a solid support, a tissue, a tissue print, and the like.

The terms "specific binding" or "specifically binding", as used herein, refers to that interaction between a protein or peptide and an agonist, an antibody and an antagonist. The interaction is dependent upon the presence of a particular structure (i.e., the antigenic determinant or epitope) of the protein recognized by the binding molecule. For example, if an antibody is specific for epitope "A", the presence of a protein containing epitope A (or free, unlabeled A) in a reaction containing labeled "A" and the antibody will reduce the amount of labeled A bound to the antibody.

The terms "stringent conditions" or "stringency", as used herein, refer to the conditions for hybridization as defined by the nucleic acid, salt, and temperature. These conditions are well known in the art and may be altered in order to identify or detect identical or related polynucleotide sequences. Numerous equivalent conditions comprising either low or high stringency depend on factors such as the length and nature of the sequence (DNA, RNA, base composition), nature of the target (DNA, RNA, base composition), milieu (in solution or immobilized on a solid substrate), concentration of salts and other components (e.g., formamide, dextran sulfate and/or polyethylene glycol), and temperature of the reactions (within a range from about 5° C. below the melting temperature of the probe to about 20° C. to 25° C. below the melting temperature). One or more factors be may be varied to generate conditions of either low or high stringency different from, but equivalent to, the above listed conditions.

The term "substantially purified", as used herein, refers to nucleic or amino acid sequences that are removed from their natural environment, isolated or separated, and are at least 60% free, preferably 75% free, and most preferably 90% free from other components with which they are naturally associated.

A "substitution", as used herein, refers to the replacement of one or more amino acids or nucleotides by different amino acids or nucleotides, respectively.

"Transformation", as defined herein, describes a process by which exogenous DNA enters and changes a recipient cell. It may occur under natural or artificial conditions using various methods well known in the art. Transformation may rely on any known method for the insertion of foreign nucleic acid sequences into a prokayotic or eukaryotic host cell. The method is selected based on the type of host cell being transformed and may include, but is not limited to, viral infection, electroporation, heat shock, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

A "variant" of HSPHH, as used herein, refers to an amino acid sequence that is altered by one or more amino acids. The variant may have "conservative" changes, wherein a substituted amino acid has similar structural or chemical properties, e.g., replacement of leucine with isoleucine. More rarely, a variant may have "nonconservative" changes, e.g., replacement of a glycine with a tryptophan. Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of a new human two human heat shock protein homologs (hereinafter referred to as HSPHH-1 and HSPHH-2, and collectively as "HSPHH"), the polynucleotides encoding HSPHH, and the use of these compositions for the diagnosis, prevention, or treatment of cancer and inflammation.

Nucleic acids encoding the HSPHH-1 of the present invention were first identified in Incyte Clone 2525691 from the brain tumor cDNA library (BRAITUT21) using a computer search for amino acid sequence alignments. A consensus sequence, SEQ ID NO:2, was derived from the following overlapping and/or extended nucleic acid sequences: Incyte Clones 2525691, (BRAITUT21), 3437994 (PENCNOT05), 946910 (RATRNOT02), 493641 (HNT2NOT01), 1798627 (COLNNOT27), 1257625 (MENITUT03), 1727303 (PROSNOT14), and sequences SAEA01927 and SAEA01723.

In one embodiment, the invention encompasses a polypeptide comprising the amino acid sequence of SEQ ID NO:1, as shown in FIGS. 1A, 1B, 1C, 1D, 1E, and 1F. HSPHH-1 is 348 amino acids in length and has a DNA J domain signature from residue $F^{45}$ to residue $Y^{64}$. HSPHH-1 has three potential casein kinase II phosphorylation sites at residues $S^{122}$, $S^{178}$, and $S^{268}$, two potential tyrosine phosphorylation sites at residues $Y^{161}$ and $Y^{183}$, and nine potential protein kinase C phosphorylation sites at residues $S^{114}$, $S^{117}$, $S^{186}$, $T^{187}$, $T^{193}$ $T^{203}$, $S^{268}$, $T^{300}$, and $T^{316}$. As shown in FIG. 2, HSPHH-1 has chemical and structural homology with human Hsp40 (GI 1816452; SEQ ID NO:5). In particular, HSPHH-1 and human Hsp40 share 61% identity. Northern analysis shows the expression of this sequence in various libraries, at least 43% of which are immortalized or cancerous and at least 30% of which involve an inflammatory response.

Nucleic acids encoding the HSPHH-2 of the present invention were first identified in Incyte Clone 3172266 from the breast tissue cDNA library (BRSTNOT18) using a computer search for amino acid sequence alignments. A consensus sequence, SEQ ID NO:4, was derived from the following overlapping and/or extended nucleic acid sequences: Incyte Clones 3172266 (BRSTNOT18), 1922858 (BRSTTUT01, and 1262291 (SYNORAT05).

In one embodiment, the invention encompasses a polypeptide comprising the amino acid sequence of SEQ ID NO:3, as shown in FIGS. 3A and 3B. HSPHH-2 is 137 amino acids in length and has three potential casein kinase II phosphorylation sites at residues $S^{30}$, $S^{50}$, and $S^{68}$, and a potential protein kinase C phosphorylation site at residue $S^{40}$. As shown in FIG. 4, HSPHH-2 has chemical and structural homology with Saccharomyces cerevisiae heat shock protein (GI 1270709; SEQ ID NO:6). In particular, HSPHH-2 and Saccharomyces cerevisiae heat shock protein share 24% identity. Northern analysis shows the expression of this sequence in various libraries, at least 57% of which are immortalized or cancerous and at least 21% of which involve an inflammatory response. Of particular note is the expression of HSPHH-2 in reproductive tissues.

The invention also encompasses HSPHH-1 variants. A preferred HSPHH-1 variant is one having at least 80%, and more preferably at least 90%, amino acid sequence identity to the HSPHH-1 amino acid sequence (SEQ ID NO:1) and which retains at least one biological, immunological or other functional characteristic or activity of HSPHH-1. A most preferred HSPHH-1 variant is one having at least 95% amino acid sequence identity to SEQ ID NO:1

The invention further encompasses HSPHH-2 variants. A preferred HSPHH-2 variant is one having at least 80%, and more preferably at least 90%, amino acid sequence identity to the HSPHH-2 amino acid sequence (SEQ ID NO:3) and which retains at least one biological, immunological or other functional characteristic or activity of HSPHH-2. A most preferred HSPHH-2 variant is one having at least 95% amino acid sequence identity to SEQ ID NO:3.

The invention also encompasses polynucleotides which encode HSPHH-1. Accordingly, any nucleic acid sequence which encodes the amino acid sequence of HSPHH-1 can be used to produce recombinant molecules which express HSPHH-1. In a particular embodiment, the invention encompasses the polynucleotide comprising the nucleic acid sequence of SEQ ID NO:2 as shown in FIGS. 1A, 1B, 1C, 1D, 1E, and 1F. The invention also encompasses a variant of a polynucleotide sequence encoding HSPHH-1. In particular, such a variant polynucleotide sequence will have at least about 80%, more preferably at least about 90%, and most preferably at least about 95% polynucleotide sequence identity to the polynucleotide sequence encoding HSPHH-1. A particular aspect of the invention encompasses a variant of SEQ ID NO:2 which has about 80%, more preferably at least about 90%, and most preferably at least about 95% polynucleotide sequence identity to SEQ ID NO:2.

The invention further encompasses polynucleotides which encode HSPHH-2. Accordingly, any nucleic acid sequence which encodes the amino acid sequence of HSPHH-2 can be used to produce recombinant molecules which express HSPHH-2. In a particular embodiment, the invention encompasses the polynucleotide comprising the nucleic acid sequence of SEQ ID NO:4 as shown in FIGS. 3A and 3B. The invention also encompasses a variant of a polynucleotide sequence encoding HSPHH-2. In particular, such a variant polynucleotide sequence will have at least about 80%, more preferably at least about 90%, and most preferably at least about 95% polynucleotide sequence identity to the polynucleotide sequence encoding HSPHH-2. A particular aspect of the invention encompasses a variant of SEQ ID NO:4 which has about 80%, more preferably at least about 90%, and most preferably at least about 95% polynucleotide sequence identity to SEQ ID NO:4.

It will be appreciated by those skilled in the art that as a result of the degeneracy of the genetic code, a multitude of nucleotide sequences encoding HSPHH, some bearing minimal homology to the nucleotide sequences of any known and naturally occurring gene, may be produced. Thus, the invention contemplates each and every possible variation of nucleotide sequence that could be made by selecting combinations based on possible codon choices. These combinations are made in accordance with the standard triplet genetic code as applied to the nucleotide sequence of naturally occurring HSPHH, and all such variations are to be considered as being specifically disclosed.

Although nucleotide sequences which encode HSPHH and its variants are preferably capable of hybridizing to the nucleotide sequence of the naturally occurring HSPHH under appropriately selected conditions of stringency, it may be advantageous to produce nucleotide sequences encoding HSPHH or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HSPHH and its derivatives without altering the encoded amino acid sequences include the production of RNA transcripts having more desirable properties, such as a greater half-life, than transcripts produced from the naturally occurring sequence.

The invention also encompasses production of DNA sequences, or fragments thereof, which encode HSPHH and its derivatives, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HSPHH or any fragment thereof.

Also encompassed by the invention are polynucleotide sequences that are capable of hybridizing to the claimed nucleotide sequences, and in particular, those shown in SEQ ID NO:2 and SEQ ID NO:4, under various conditions of stringency as taught in Wahl, G. M. and S. L. Berger (1987; Methods Enzymol. 152: 399–407) and Kimmel, A. R. (1987; Methods Enzymol. 152: 507–511).

Methods for DNA sequencing which are well known and generally available in the art and may be used to practice any of the embodiments of the invention. The methods may employ such enzymes as the Klenow fragment of DNA polymerase I, Sequenase® (US Biochemical Corp, Cleveland, Ohio), Taq polymerase (Perkin Elmer), thermostable T7 polymerase (Amersham, Chicago, Ill.), or combinations of polymerases and proofreading exonucleases such as those found in the ELONGASE Amplification System marketed by Gibco/BRL (Gaithersburg, Md.). Preferably, the process is automated with machines such as the Hamilton Micro Lab 2200 (Hamilton, Reno, Nev.), Peltier Thermal Cycler (PTC200; MJ Research, Watertown, Mass.) and the ABI Catalyst and 373 and 377 DNA Sequencers (Perkin Elmer).

The nucleic acid sequences encoding HSPHH may be extended utilizing a partial nucleotide sequence and employing various methods known in the art to detect upstream sequences such as promoters and regulatory elements. For example, one method which may be employed, "restriction-site" PCR, uses universal primers to retrieve unknown sequence adjacent to a known locus (Sarkar, G. (1993) PCR Methods Applic. 2: 318–322). In particular, genomic DNA is first amplified in the presence of primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region (Triglia, T. et al. (1988) Nucleic Acids Res. 16: 8186). The primers may be designed using commercially available software such as OLIGO 4.06 Primer Analysis software (National Biosciences Inc., Plymouth, Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Another method which may be used is capture PCR which involves PCR amplification of DNA fragments adjacent to a known sequence in human and yeast artificial chromosome DNA (Lagerstrom, M. et al. (1991) PCR Methods Applic. 1: 111–119). In this method, multiple restriction enzyme digestions and ligations may also be used to place an engineered double-stranded sequence into an unknown fragment of the DNA molecule before performing PCR.

Another method which may be used to retrieve unknown sequences is that of Parker, J. D. et al. (1991; Nucleic Acids Res. 19: 3055–3060). Additionally, one may use PCR, nested primers, and PromoterFinder™ libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable, in that they will contain more sequences which contain the 5' regions of genes. Use of a randomly primed library may be especially preferable for situations in which an oligo d(T)

library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and detection of the emitted wavelengths by a charge coupled devise camera. Output/light intensity may be converted to electrical signal using appropriate software (e.g. Genotyper™ and Sequence Navigator™, Perkin Elmer) and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HSPHH may be used in recombinant DNA molecules to direct expression of HSPHH, fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HSPHH.

As will be understood by those of skill in the art, it may be advantageous to produce HSPHH-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HSPHH encoding sequences for a variety of reasons, including but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HSPHH may be ligated to a heterologous sequence to encode a fusion protein. For example, to screen peptide libraries for inhibitors of HSPHH activity, it may be useful to encode a chimeric HSPHH protein that can be recognized by a commercially available antibody. A fusion protein may also be engineered to contain a cleavage site located between the HSPHH encoding sequence and the heterologous protein sequence, so that HSPHH may be cleaved and purified away from the heterologous moiety.

In another embodiment, sequences encoding HSPHH may be synthesized, in whole or in part, using chemical methods well known in the art (see Caruthers, M. H. et al. (1980) Nucl. Acids Res. Symp. Ser. 215–223, Horn, T. et al. (1980) Nucl. Acids Res. Symp. Ser. 225–232). Alternatively, the protein itself may be produced using chemical methods to synthesize the amino acid sequence of HSPHH, or a fragment thereof. For example, peptide synthesis can be performed using various solid-phase techniques (Roberge, J. Y. et al. (1995) Science 269: 202–204) and automated synthesis may be achieved, for example, using the ABI 431A Peptide Synthesizer (Perkin Elmer).

The newly synthesized peptide may be substantially purified by preparative high performance liquid chromatography (e.g., Creighton, T. (1983) *Proteins, Structures and Molecular Principles,* WH Freeman and Co., New York, N.Y.). The composition of the synthetic peptides may be confirmed by amino acid analysis or sequencing (e.g., the Edman degradation procedure; Creighton, supra). Additionally, the amino acid sequence of HSPHH, or any part thereof, may be altered during direct synthesis and/or combined using chemical methods with sequences from other proteins, or any part thereof, to produce a variant polypeptide.

In order to express a biologically active HSPHH, the nucleotide sequences encoding HSPHH or functional equivalents, may be inserted into appropriate expression vector, i.e., a vector which contains the necessary elements for the transcription and translation of the inserted coding sequence.

Methods which are well known to those skilled in the art may be used to construct expression vectors containing sequences encoding HSPHH and appropriate transcriptional and translational control elements. These methods include in vitro recombinant DNA techniques, synthetic techniques, and in vivo genetic recombination. Such techniques are described in Sambrook, J. et al. (1989) *Molecular Cloning, A Laboratory Manual,* Cold Spring Harbor Press, Plainview, N.Y., and Ausubel, F. M. et al. (1989) *Current Protocols in Molecular Biology,* John Wiley & Sons, New York, N.Y.

A variety of expression vector/host systems may be utilized to contain and express sequences encoding HSPHH. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus, CaMV; tobacco mosaic virus, TMV) or with bacterial expression vectors (e.g., Ti or pBR322 plasmids); or animal cell systems. The invention is not limited by the host cell employed.

The "control elements" or "regulatory sequences" are those non-translated regions of the vector—enhancers, promoters, 5' and 3' untranslated regions—which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the Bluescript® phagemid (Stratagene, LaJolla, Calif.) or pSport1™ plasmid (Gibco BRL) and the like may be used. The baculovirus polyhedrin promoter may be used in insect cells. Promoters or enhancers derived from the genomes of plant cells (e.g., heat shock, RUBISCO; and storage protein genes) or from plant viruses (e.g., viral promoters or leader sequences) may be cloned into the vector. In mammalian cell systems, promoters from mammalian genes; or from mammalian viruses are preferable. If it is necessary to generate a cell line that contains multiple copies of the sequence encoding HSPHH, vectors based on SV40 or EBV may be used with an appropriate selectable marker.

In bacterial systems, a number of expression vectors may be selected depending upon the use intended for HSPHH.

For example, when large quantities of HSPHH are needed for the induction of antibodies, vectors which direct high level expression of fusion proteins that are readily purified may be used. Such vectors include, but are not limited to, the multifunctional *E. coli* cloning and expression vectors such is Bluescript® (Stratagene), in which the sequence encoding HSPHH may be ligated into the vector in frame with sequences for the amino-terminal Met and the subsequent 7 residues of β-galactosidase so that a hybrid protein is produced; pIN vectors (Van Heeke, G. and S. M. Schuster (1989) J. Biol. Chem. 264: 5503–5509); and the like. pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast, *Saccharomvces cerevisiae,* a number of vectors containing constitutive or inducible promoters such as alpha factor, alcohol oxidase, and PGH may be used. For reviews, see Ausubel et al. (supra) and Grant et al. (1987) Methods Enzymol. 153: 516–544.

In cases where plant expression vectors are used, the expression of sequences encoding HSPHH may be driven by any of a number of promoters. For example, viral promoters such as the 35S and 19S promoters of CaMV may be used alone or in combination with the omega leader sequence from TMV (Takamatsu, N. (1987) EMBO J. 6: 307–311). Alternatively, plant promoters such as the small subunit of RUBISCO or heat shock promoters may be used (Coruzzi, G. et al. (1984) EMBO J. 3: 1671–1680; Broglie, R. et al. (1984) Science 224: 838–843; and Winter, J. et al. (1991) Results Probl. Cell Differ. 17: 85–105). These constructs can be introduced into plant cells by direct DNA transformation or pathogen-mediated transfection. Such techniques are described in a number of generally available reviews (see, for example, Hobbs, S. or Murry, L. E. in McGraw Hill *Yearbook of Science and Technology* (1992) McGraw Hill, New York, N.Y.; pp. 191–196.

An insect system may also be used to express HSPHH. For example, in one such system, *Autographa californica* nuclear polyhedrosis virus (AcNPV) is used as a vector to express foreign genes in *Spodoptera frugiperda* cells or in Trichoplusia larvae. The sequences encoding HSPHH may be cloned into a non-essential region of the virus, such as the polyhedrin gene, and placed under control of the polyhedrin promoter. Successful insertion of HSPHH will render the polyhedrin gene inactive and produce recombinant virus lacking coat protein. The recombinant viruses may then be used to infect, for example, *S. frugiperda* cells or Trichoplusia larvae in which HSPHH may be expressed (Engelhard, E. K. et al. (1994) Proc. Nat. Acad. Sci. 91: 3224–3227).

In mammalian host cells, a number of viral-based expression systems may be utilized. In cases where an adenovirus is used as an expression vector, sequences encoding HSPHH may be ligated into an adenovirus transcription/translation complex consisting of the late promoter and tripartite leader sequence. Insertion in a non-essential E1 or E3 region of the viral genome may be used to obtain a viable virus which is capable of expressing HSPHH in infected host cells (Logan, J. and Shenk, T. (1984) Proc. Natl. Acad. Sci. 81: 3655–3659). In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of 6 to 10M are constructed and delivered via conventional delivery method (liposomes, polycationic amino polymers, or vesicles) for therapeutic purposes.

Specific initiation signals may also be used to achieve more efficient translation of sequences encoding HSPHH. Such signals include the ATG initiation codon and adjacent sequences. In cases where sequences encoding HSPHH, its initiation codon, and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers which are appropriate for the particular cell system which is used, such as those described in the literature (Scharf, D. et al. (1994) Results Probl. Cell Differ. 20: 125–162).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding and/or function. Different host cells which have specific cellular machinery and characteristic mechanisms for post-translational activities (e.g., CHO, HeL,a, MDCK, HEK293, and WI38), are available from the American Type Culture Collection (ATCC; Bethesda, Md.) and may be chosen to ensure the correct modification and processing of the foreign protein.

For long-term, high-yield production of recombinant proteins, stable expression is preferred. For example, cell lines which stably express HSPHH may be transformed using expression vectors which may contain viral origins of replication and/or endogenous expression elements and a selectable marker gene on the same or on a separate vector. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex viris thymidine kinase (Wigler, M. et al. (1977) Cell 11: 223–32) and adenine phosphoribosyltransferase (Lowy, I. et al. (1980) Cell 22: 817–23) genes which can be employed in tk⁻ or aprt⁻ cells, respectively. Also, antimetabolite, antibiotic or herbicide resistance can be used as the basis for selection; for example, dhfr which confers resistance to methotrexate (Wigler, M. et al. (1980) Proc. Natl. Acad. Sci. 77: 3567–70); npt, which confers resistance to the aminoglycosides neomycin and G-418 (Colbere-Garapin, F. et al (1981) J. Mol. Biol. 150: 1–14) and al or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman, S. C. and R. C. Mulligan (1988) Proc. Natl. Acad. Sci. 85: 8047–51). Recently, the use of visible markers has gained popularity with such markers as anthocyanins, β glucuronidase and its substrate GUS, and luciferase and its substrate luciferin, being widely used not only to identify transformants, but also to quantify the amount of transient or stable protein expression attributable to a specific vector system (Rhodes, C. A. et al. (1995) Methods Mol. Biol. 55: 121–131).

Although the presence/absence of marker gene expression suggests that the gene of interest is also present, its presence and expression may need to be confirmed. For example, if the sequence encoding HSPHH is inserted within a marker gene sequence, transformed cells containing sequences encoding HSPHH can be identified by the absence of marker gene function. Alternatively, a marker gene can be placed in tandem with a sequence encoding HSPHH under the control of a single promoter. Expression of the marker gene in response to induction or selection usually indicates expression of the tandem gene as well.

Alternatively, host cells which contain the nucleic acid sequence encoding HSPHH and express HSPHH may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein.

The presence of polynucleotide sequences encoding HSPHH can be detected by DNA-DNA or DNA-RNA hybridization or amplification using probes or fragments or fragments of polynucleotides encoding HSPHH. Nucleic acid amplification based assays involve the use of oligonucleotides or oligomers based on the sequences encoding HSPHH to detect transformants containing DNA or RNA encoding HSPHH.

A variety of protocols for detecting and measuring the expression of HSPHH, using either polyclonal or monoclonal antibodies specific for the protein are known in the art. Examples include enzyme-linked immunosorbent assay (ELISA), radioimmunoassay (RIA), and fluorescence activated cell sorting (FACS). A two-site, monoclonal-based immunoassay utilizing monoclonal antibodies reactive to two non-interfering epitopes on HSPHH is preferred, but a competitive binding assay may be employed. These and other assays are described, among other places, in Hampton, R. et al. (1990; *Serological Methods, a Laboratory Manual*, APS Press, St Paul, Minn.) and Maddox, D. E. et al. (1983; J. Exp. Med. 158: 1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HSPHH include oligolabeling, nick translation, end-labeling or PCR amplification using a labeled nucleotide. Alternatively, the sequences encoding HSPHH, or any fragments thereof may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits (Pharmacia & Upjohn, (Kalamazoo, Minn.); Promega (Madison Wis.); and U.S. Biochemical Corp., Cleveland, Ohio). Suitable reporter molecules or labels, which may be used for ease of detection, include radionuclides, enzymes, fluorescent, chemiluminescent, or chromogenic agents as well as substrates, cofactors, inhibitors, magnetic particles, and the like.

Host cells transformed with nucleotide sequences encoding HSPHH may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HSPHH may be designed to contain signal sequences which direct secretion of HSPHH through a prokaryotic or eukaryotic cell membrane. Other constructions may be used to join sequences encoding HSPHH to nucleotide sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences such as those specific for Factor XA or enterokinase (Invitrogen, San Diego, Calif.) between the purification domain and HSPHH may be used to facilitate purification. One such expression vector provides for expression of a fusion protein containing HSPHH and a nucleic acid encoding 6 histidine residues preceding a thioredoxin or an enterokinase cleavage site. The histidine residues facilitate purification on IMAC (immobilized metal ion affinity chromatography as described in Porath, J. et al. (1992, Prot. Exp. Purif. 3: 263–281) while the enterokinase cleavage site provides a means for purifying HSPHH from the fusion protein. A discussion of vectors which contain fusion proteins is provided in Kroll, D. J. et al. (1993; DNA Cell Biol. 12: 441–453).

In addition to recombinant production, fragments of HSPHH may be produced by direct peptide synthesis using solid-phase techniques Merrifield J. (1963) J. Am. Chem. Soc. 85: 2149–2154). Protein synthesis may be performed using manual techniques or by automation. Automated synthesis may be achieved, for example, using Applied Biosystems 431A Peptide Synthesizer (Perkin Elmer). Various fragments of HSPHH may be chemically synthesized separately and combined using chemical methods to produce the full length molecule.

Therapeutics

Chemical and structural homology exists between HSPHH-1 and human Hsp40 (GI 1816452), and between HSPHH-2 and *Saccharomyces cerevisiae* heat shock protein (GI 1279709). In addition, HSPHH-1 and HSPHH-2 are expressed in cancer and inflamed tissues. Therefore, HSPHH appears to play a role in cancer and inflammation.

In one embodiment, an antagonist of HSPHH-1 may be administered to a subject to prevent or treat a cancer. Such cancers may include, but are not limited to, adenocarcinoma, leukemia, lymphoma, melanoma, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HSPHH-1 may be used directly as an antagonist or indirectly as a targeting or delivery mechanism for bringing a pharmaceutical agent to cells or tissue which express HSPHH-1.

In another embodiment, a vector expressing the complement of the polynucleotide encoding HSPHH-1 may be administered to a subject to treat or prevent disorders including, but not limited to, those cancers described above.

In one embodiment, an antagonist of HSPHH-1 may be administered to a subject to prevent or treat inflammation. Inflammation may be associated with, but are not limited to, disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, pyelonephritis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma.

In another embodiment, a vector expressing the complement of the polynucleotide encoding HSPHH-1 may be administered to a subject to treat or prevent inflammation, and in particular, the disorders provided above with which inflammation is associated.

In one embodiment, an antagonist of HSPHH-2 may be administered to a subject to prevent or treat a cancer. Such cancers may include, but are not limited to, adenocarcinoma, leukemia, lymphoma, melanoma, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HSPHH-2 may be used directly as an antagonist or indirectly as a targeting or delivery mechanism for bringing a pharmaceutical agent to cells or tissue which express HSPHH-2.

In another embodiment, a vector expressing the complement of the polynucleotide encoding HSPHH-2 may be administered to a subject to treat or prevent disorders including, but not limited to, those cancers described above.

In one embodiment, an antagonist of HSPHH-2 may be administered to a subject to prevent or treat inflammation. Inflammation may be associated with, but are not limited to, disorders such as AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, pyelonephritis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma.

In another embodiment, a vector expressing the complement of the polynucleotide encoding HSPHH-2 may be administered to a subject to treat or prevent inflammation, and in particular, the disorders provided above with which inflammation is associated.

In other embodiments, any of the proteins, antagonists, antibodies, agonists, complementary sequences or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HSPHH may be produced using methods which are generally known in the art. In particular, purified HSPHH may be used to produce antibodies or to screen libraries of pharmaceutical agents to identify those which specifically bind HSPHH.

Antibodies to HSPHH may be generated using methods that are well known in the art. Such antibodies may include, but are not limited to, polyclonal, monoclonal, chimeric, single chain, Fab fragments, and fragments produced by a Fab expression library. Neutralizing antibodies, (i.e., those which inhibit dimer formation) are especially preferred for therapeutic use.

For the production of antibodies, various hosts including goats, rabbits, rats, mice, humans, and others, may be immunized by injection with HSPHH or any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, keyhole limpet hemocyanin, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HSPHH have an amino acid sequence consisting of at least five amino acids and more preferably at least 10 amino acids. It is also preferable that they are identical to a portion of the amino acid sequence of the natural protein, and they may contain the entire amino acid sequence of a small, naturally occurring molecule. Short stretches of HSPHH amino acids may be fused with those of another protein such as keyhole limpet hemocyanin and antibody produced against the chimeric molecule.

Monoclonal antibodies to HSPHH may be prepared using any technique which provides for the production of antibody molecules by continuous cell lines in culture. These include, but are not limited to, the hybridoma technique, the human B-cell hybridoma technique, and the EBV-hybridoma technique (Kohler, G. et al. (1975) Nature 256: 495–497; Kozbor, D. et al. (1985) J. Immunol. Methods 81: 31–42; Cote, R. J. et al. (1983) Proc. Natl. Acad. Sci. 80: 2026–2030; Cole, S. P. et al. (1984) Mol. Cell Biol. 62: 109–120).

In addition, techniques developed for the production of "chimeric antibodies", the splicing of mouse antibody genes to human antibody genes to obtain a molecule with appropriate antigen specificity and biological activity can be used (Morrison, S. L. et al. (1984) Proc. Natl. Acad. Sci. 81: 6851–6855; Neuberger, M. S. et al. (1984) Nature 312: 604–608; Takeda, S. et al. (1985) Nature 314: 452–454). Alternatively, techniques described for the production of single chain antibodies may be adapted, using methods known in the art, to produce HSPHH-specific single chain antibodies. Antibodies with related specificity, but of distinct idiotypic composition, may be generated by chain shuffling from random combinatorial immunoglobin libraries (Burton D. R. (1991) Proc. Natl. Acad. Sci. 88: 11120–3).

Antibodies may also be produced by inducing in vivo production in the lymphocyte population or by screening immunoglobulin libraries or panels of highly specific binding reagents as disclosed in the literature (Orlandi, R. et al. (1989) Proc. Natl. Acad. Sci. 86: 3833–3837; Winter, G. et al. (1991) Nature 349: 293–299).

Antibody fragments which contain specific binding sites for HSPHH may also be generated. For example, such fragments include, but are not limited to, the F(ab)2 fragments which can be produced by pepsin digestion of the antibody molecule and the Fab fragments which can be generated by reducing the disulfide bridges of the F(ab)2 fragments. Alternatively, Fab expression libraries may be constructed to allow rapid and easy identification of monoclonal Fab fragments with the desired specificity (Huse, W. D. et al. (1989) Science 254: 1275–1281).

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HSPHH and its specific antibody. A two-site, monoclonal-based immunoassay utilizing monoclonal antibodies reactive to two non-interfering HSPHH epitopes is preferred, but a competitive binding assay may also be employed (Maddox, supra).

In another embodiment of the invention, the polynucleotides encoding HSPHH, or any fragment or complement thereof, may be used for therapeutic purposes. In one aspect, the complement of the polynucleotide encoding HSPHH may be used in situations in which it would be desirable to block the transcription of the mRNA. In particular, cells may be transformed with sequences complementary to polynucleotides encoding HSPHH. Thus, complementary molecules or fragments may be used to modulate HSPHH activity, or to achieve regulation of gene function. Such technology is now well known in the art, and sense or antisense oligonucleotides or larger fragments, can be designed from various locations along the coding or control regions of sequences encoding HSPHH.

Expression vectors derived from retro viruses, adenovirus, herpes or vaccinia viruses, or from various bacterial plasmids may be used for delivery of nucleotide sequences to the targeted organ, tissue or cell population. Methods which are well known to those skilled in the art can be used to construct vectors which will express nucleic acid sequence which is complementary to the polynucleotides of the gene encoding HSPHH. These techniques are described both in Sambrook et al. (supra) and in Ausubel et al. (supra).

Genes encoding HSPHH can be turned off by transforming a cell or tissue with expression vectors which express high levels of a polynucleotide or fragment thereof which encodes HSPHH. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector and even longer if appropriate replication elements are part of the vector system.

As mentioned above, modifications of gene expression can be obtained by designing complementary sequences or antisense molecules (DNA, RNA, or PNA) to the control, 5' or regulatory regions of the gene encoding HSPHH (signal sequence, promoters, enhancers, and introns). Oligonucleotides derived from the transcription initiation site, e.g., between positions -10 and +10 from the start site, are preferred. Similarly, inhibition can be achieved using "triple helix" base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature (Gee, J. E. et al. (1994) In: Huber, B. E. and B. I. Carr, *Molecular and Immunologic Approaches,* Futura Publishing Co., Mt. Kisco, N.Y.). The complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. Examples which may be used include engineered hammerhead motif ribozyme molecules that can specifically and efficiently catalyze endonucleolytic cleavage of sequences encoding HSPHH.

Specific ribozyme cleavage sites within any potential RNA target are initially identified by scanning the target molecule for ribozyme cleavage sites which include the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary ogligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HSPHH. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracelluar stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections or polycationic amino polymers (Goldman, C. K. et al. (1997) Nature Biotechnology 15: 462–66; incorporated herein by reference) may be achieved using methods which are well known in the art.

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical composition, in conjunction with a pharmaceutically acceptable carrier, for any of the therapeutic effects discussed above. Such pharmaceutical compositions may consist of HSPHH, antibodies to HSPHH, mimetics, agonists, antagonists, or inhibitors of HSPHH. The compositions may be administered alone or in combination with at least one other agent, such as stabilizing compound, which may be administered in any sterile, biocompatible pharmaceutical carrier, including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically-acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with a filler or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers may also be used for delivery. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation may be a lyophilized powder which may contain any or all of the following: 1–50 mM histidine, 0.1%–2% sucrose, and 2–7% mannitol, at a pH range of 4.5 to 5.5, that is combined with buffer prior to use.

After pharmaceutical compositions have been prepared, they can be placed in an appropriate container and labeled for treatment of an indicated condition. For administration of HSPHH, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, e.g., of neoplastic cells, or in animal remodels, usually mice, rabbits, dogs, or pigs. The animal model may also be used to determine the appropriate concentration range and route of administration. Such information can then be used to determine useful doses and routes for administration in humans.

A therapeutically effective dose refers to that amount of active ingredient, for example HSPHH or fragments thereof, antibodies of HSPHH, agonists, antagonists or inhibitors of HSPHH, which ameliorates the symptoms or condition. Therapeutic efficacy and toxicity may be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active moiety or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HSPHH may be used for the diagnosis of conditions or diseases characterized by expression of HSPHH, or in assays to monitor patients being treated with HSPHH, agonists, antagonists or inhibitors. The antibodies useful for diagnostic purposes may be prepared in the same manner as those described above for therapeutics. Diagnostic assays for HSPHH include methods which utilize the antibody and a label to detect HSPHH in human body fluids or extracts of cells or tissues. The antibodies may be used with or without modification, and may be labeled by joining them, either covalently or non-covalently, with a reporter molecule. A wide variety of reporter molecules which are known in the art may be used, several of which are described above.

A variety of protocols including ELISA, RIA, and FACS for measuring HSPHH are known in the art and provide a basis for diagnosing altered or abnormal levels of HSPHH expression. Normal or standard values for HSPHH expression are established by combining body fluids or cell extracts taken from normal mammalian subjects, preferably human, with antibody to HSPHH under conditions suitable for complex formation The amount of standard complex formation may be quantified by various methods, but preferably by photometric, means. Quantities of HSPHH expressed in subject, control and disease, samples from biopsied tissues are compared with the standard values. Deviation between standard and subject values establishes the parameters for diagnosing disease.

In another embodiment of the invention, the polynucleotides encoding HSPHH may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HSPHH may be correlated with disease. The diagnostic assay may be used to distinguish between absence, presence, and excess expression of HSPHH, and to monitor regulation of HSPHH levels during therapeutic intervention.

In one aspect, hybridization with PCR probes which are capable of detecting polynucleotide sequences, including genomic sequences, encoding HSPHH or closely related molecules, may be used to identify nucleic acid sequences which encode HSPHH. The specificity of the probe, whether it is made from a highly specific region, e.g., 10 unique nucleotides in the 5' regulatory region, or a less specific region, e.g., especially in the 3' coding region, and the stringency of the hybridization or amplification (maximal, high, intermediate, or low) will determine whether the probe identifies only naturally occurring sequences encoding HSPHH, alleles, or related sequences.

Probes may also be used for the detection of related sequences, and should preferably contain at least 50% of the nucleotides from any of the HSPHH encoding sequences. The hybridization probes of the subject invention may be DNA or RNA and derived from the nucleotide sequence of SEQ ID NO:2 and SEQ ID NO:4 or from genomic sequence including promoter, enhancer elements, and introns of the naturally occurring HSPHH.

Means for producing specific hybridization probes for DNAs encoding HSPHH include the cloning of nucleic acid sequences encoding HSPHH or HSPHH derivatives into vectors for the production of mRNA probes. Such vectors are known in the art, commercially available, and may be used to synthesize RNA probes in vitro by means of the addition of the appropriate RNA polymerases and the appropriate labeled nucleotides. Hybridization probes may be labeled by a variety of reporter groups, for example, radionuclides such as 32P or 35S, or enzymatic labels, such as alkaline phosphatase coupled to the probe via avidin/biotin coupling systems, and the like.

Polynucleotide sequences encoding HSPHH may be used for the diagnosis of conditions or disorders which are associated with expression of HSPHH. Examples of such conditions or disorders include adenocarcinoma, leukemia, lymphoma, melanoma, myeloma, sarcoma, and teratocarcinoma and particularly cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus; and inflammation associated with conditions and disorders including AIDS, Addison's disease, adult respiratory distress syndrome, allergies, anemia, asthma, atherosclerosis, bronchitis, cholecystitis, Crohn's disease, ulcerative colitis, atopic dermatitis, dermatomyositis, diabetes mellitus, emphysema, erythema nodosum, atrophic gastritis, glomerulonephritis, gout, Graves' disease, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, pyelonephritis, rheumatoid arthritis, scleroderma, Sjögren's syndrome, and autoimmune thyroiditis; complications of cancer, hemodialysis, and extracorporeal circulation; viral, bacterial, fungal, parasitic, protozoal, and helminthic infections; and trauma. The polynucleotide sequences encoding HSPHH may be used in Southern or northern analysis, dot blot, or other membrane-based technologies; in PCR technologies; or in dipstick, pin, ELISA assays or microarrays utilizing fluids or tissues from patient biopsies to detect altered HSPHH expression. Such qualitative or quantitative methods are well known in the art.

In a particular aspect, the nucleotide sequences encoding HSPHH may be useful in assays that detect activation or induction of various cancers, particularly those mentioned above. The nucleotide sequences encoding HSPHH may be labeled by standard methods, and added to a fluid or tissue sample from a patient under conditions suitable for the formation of hybridization complexes. After a suitable incubation period, the sample is washed and the signal is quantitated and compared with a standard value. If the amount of signal in the biopsied or extracted sample is significantly altered from that of a comparable control sample, the nucleotide sequences have hybridized with nucleotide sequences in the sample, and the presence of altered levels of nucleotide sequences encoding HSPHH in the sample indicates the presence of the associated disease. Such assays may also be used to evaluate the efficacy of a particular therapeutic treatment regimen in animal studies, in clinical trials, or in monitoring the treatment of an individual patient.

In order to provide a basis for the diagnosis of disease associated with expression of HSPHH, a normal or standard profile for expression is established. This may be accomplished by combining body fluids or cell extracts taken from normal subjects, either animal or human, with a sequence, or a fragment thereof, which encodes HSPHH, under conditions suitable for hybridization or amplification. Standard hybridization may be quantified by comparing the values obtained from normal subjects with those from an experiment where a known amount of a substantially purified polynucleotide is used. Standard values obtained from normal samples may be compared with values obtained from samples from patients who are symptomatic for disease. Deviation between standard and subject values is used to establish the presence of disease.

Once disease is established and a treatment protocol is initiated, hybridization assays may be repeated on a regular basis to evaluate whether the level of expression in the patient begins to approximate that which is observed in the normal patient. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HSPHH may involve the use of PCR. Such oligomers may be chemically synthesized, generated enzymatically, or produced in vitro. Oligomers will preferably consist of two nucleotide sequences, one with sense orientation (5'→3') and another with antisense (3'←5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Methods which may also be used to quantitate the expression of HSPHH include radiolabeling or biotinylating nucleotides, coamplification of a control nucleic acid, and standard curves onto which the experimental results are interpolated (Melby, P. C. et al. (1993) J. Immunol. Methods, 159: 235–244; Duplaa, C. et al. (1993) Anal. Biochem. 229–236). The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer Fragments derived from any of the polynucleotide sequences described herein may be used as targets in a microarray. The microarray can be used to monitor the expression level of large numbers of genes simultaneously (to produce a transcript image), and to identify genetic variants, mutations and polymorphisms. This information may be used to determine gene function, understanding the genetic basis of disease, diagnosing disease, and in developing and in monitoring the activities of therapeutic agents.

In further embodiments, oligonucleotides or longer fragments derived from any of the polynucleotide sequences described herein may be used as targets in a microarray. The microarray can be used to monitor the expression level of large numbers of genes simultaneously (to produce a transcript image), and to identify genetic variants, mutations and polymorphisms. This information may be used to determine gene function, understanding the genetic basis of disease, diagnosing disease, and in developing and in monitoring the activities of therapeutic agents.

In one embodiment, the microarray is prepared and used according to the methods described in PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference.

The microarray is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray, it may be preferable to use oligonucleotides which are only 7–10 nucleotides in length. The microarray may contain oligonucleotides which cover the known 5', or 3', sequence, sequential oligonucleotides which cover the full length sequence; or unique oligonucleotides selected from particular areas along the length of the sequence. Polynucleotides used in the microarray may be oligonucleotides that are specific to a gene or genes of interest in which at least a fragment of the sequence is known or that are specific to one or more unidentified cDNAs which are common to a particular cell type, developmental or disease state.

In order to produce oligonucleotides to a known sequence for a microarray, the gene of interest is examined using a computer algorithm which starts at the 5' or more preferably at the 3' end of the nucleotide sequence. The algorithm identifies oligomers of defined length that are unique to the gene, have a GC content within a range suitable for hybridization, and lack predicted secondary structure that may interfere with hybridization. In certain situations it may be appropriate to use pairs of oligonucleotides on a microarray. The "pairs" will be identical, except for one nucleotide which preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536 or 6144 oligonucleotides, or any other number between two and one million which lends itself to the efficient use of commercially available instrumentation.

In order to conduct sample analysis using a microarray, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray so that the probe sequences hybridize to complementary oligonucleotides of the microarray. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large scale correlation studies on the sequences, mutations, variants, or polymorphisms among samples (Heller, R. A. et al. (1997 Proc. Natl. Acad. Sci. 94: 2150–2155).

In another embodiment of the invention, the nucleic acid sequences which encode HSPHH may also be used to generate hybridization probes which are useful for mapping the naturally occurring genomic sequence. The sequences may be mapped to a particular chromosome, to a specific region of a chromosome or to artificial chromosome constructions, such as human artificial chromosomes (HACs), yeast artificial chromosomes (YACs), bacterial artificial chromosomes (BACs), bacterial P1 constructions or single chromosome cDNA libraries as reviewed in Price, C. M. (1993) Blood Rev. 7: 127–134, and Trask, B. J. (1991) Trends Genet. 7: 149–154.

Fluorescent in situ hybridization (FISH as described in Verma et al. (1988) *Human Chromosomes: A Manual of Basic Techniques,* Pergamon Press, New York, N.Y.) may be correlated with other physical chromosome mapping techniques and genetic map data. Examples of genetic map data can be found in various scientific journals or at Online Mendelian Inheritance in Man (OMIM). Correlation between the location of the gene encoding HSPHH on a physical chromosomal map and a specific disease, or predisposition to a specific disease, may help delimit the region of DNA associated with that genetic disease. The nucleotide sequences of the subject invention may be used to detect differences in gene sequences between normal, carrier, or affected individuals.

In situ hybridization of chromosomal preparations and physical mapping techniques such as linkage analysis using established chromosomal markers may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, for example, AT to 11q22–23 (Gatti, R. A. et al. (1988) Nature 336: 577–580), any sequences mapping to that area may represent associated or regulatory genes for further investigation. The nucleotide sequence of the subject invention may also be used to detect differences in the chromosomal location due to translocation, inversion, etc. among normal, carrier, or affected individuals.

In another embodiment of the invention, HSPHH, its catalytic or immunogenic fragments or oligopeptides thereof, can be used for screening libraries of compounds in any of a variety of drug screening techniques. The fragment employed in such screening may be free in solution, affixed to a solid support, borne on a cell surface, or located intracellularly. The formation of binding complexes, between HSPHH and the agent being tested, may be measured.

Another technique for drug screening which may be used provides for high throughput screening of compounds having suitable binding affinity to the protein of interest as described in published PCT application WO84/03564. In this method, as applied to HSPHH large numbers of different small test compounds are synthesized on a solid substrate, such as plastic pins or some other surface. The test compounds are reacted with HSPHH, or fragments thereof, and washed. Bound HSPHH is then detected by methods well known in the art. Purified HSPHH can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HSPHH specifically compete with a test compound for binding HSPHH. In this manner, the antibodies can be used to detect the presence of any peptide which shares one or more antigenic determinants with HSPHH.

In additional embodiments, the nucleotide sequences which encode HSPHH may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I BRAITUT21 and BRSTNOT18 cDNA Library Construction

The BRAITUT21 cDNA library was constructed from cancerous brain tissue obtained from a 61-year-old female (specimen #0785; Mayo Clinic, Rochester, Minn.) during a cerebral meningeal excision. Pathology indicated subfrontal meningothelial meningioma with no atypia. Analysis of ethmoid tissue and mucosal tissue indicated meningioma. The patient presented with headache, an unspecified form of epilepsy and a disturbance of sensation of smell and taste. Patient history included hyperlipidemia, depressive disorder, irritable bowel, skin cancer of the leg, fibromyalgia, nosebleeds, tobacco and alcohol use, and a normal delivery.

The BRSTNOT18 cDNA library was constructed from diseased breast tissue obtained from a 57-year old female (specimen #0618; Mayo Clinic, Rochester, Minn.). The tissue showed mildly proliferative breast disease. Patient history included breast cancer, osteoarthritis, and a normal delivery. Previous surgeries included an open breast biopsy and an adenotonsillectomy. Patient medications included Estraderm patch and Provera. Family history included Type II diabetes in the father, gallbladder cancer in the mother, and breast cancer and chronic lymphocytic leukemia in a sibling.

For the preparation of both libraries, the frozen tissue was homogenized and lysed in Trizol reagent (1 gm tissue/10 ml Trizol; Cat. #10296–028; Gibco/BRL) using a Brinkmann Homogenizer Polytron PT-3000 (Brinkmann Instruments, Westbury, N.Y.). After a brief incubation on ice, chloroform was added (1:5 v/v) and the lysate was centrifuged. The upper chloroform layer was removed to a fresh tube and the RNA extracted with isopropanol, resuspended in DEPC-treated water, and DNase treated for 25 min at 37° C. The RNA was re-extracted once with acid phenol-chloroform pH 4.7 and precipitated using 0.3 M sodium acetate and 2.5 volumes ethanol. The mRNAs were then isolated using the Qiagen Oligotex kit (QIAGEN, Inc., Chatsworth, Calif.) and used to construct the cDNA library.

The mRNA was handled according to the recommended protocols in the SuperScript Plasmid System for cDNA Synthesis and Plasmid Cloning (Cat. #18248-013, Gibco/BRL). The cDNAs were fractionated on a Sepharose CL4B column (Cat. #275105-01; Pharmacia), and those cDNAs exceeding 400 bp were ligated into pINCY 1. The plasmid pINCY 1 was subsequently transformed into DH5a™ competent cells (Cat. #18258-012; Gibco/BRL).

II Isolation and Sequencing of cDNA clones

Plasmid DNA was released from the cells and purified using the REAL Prep 96 Plasmid Kit (Catalog #26173; QIAGEN, Inc.). The recommended protocol was employed except for the following changes: 1) the bacteria were cultured in 1 ml of sterile Terrific Broth (Catalog #22711, Gibco/BRL) with carbenicillin at 25 mg/L and glycerol at 0.4%; 2) after inoculation, the cultures were incubated for 19 hours and at the end of incubation, the cells were lysed with 0.3 ml of lysis buffer; and 3) following isopropanol precipitation, the plasmid DNA pellet was resuspended in 0.1 ml of distilled water. After the last step in the protocol, samples were transferred to a 96-well block for storage at 4° C.

The cDNAs were sequenced by the method of Sanger et al. (1975, J. Mol. Biol. 94: 441f), using a Hamilton Micro Lab 2200 (Hamilton, Reno, Nev.) in combination with Peltier Thermal Cyclers (PTC200 from MJ Research, Watertown, Mass.) and Applied Biosystems 377 DNA Sequencing Systems.

III Homology Searching of cDNA Clones and Their Deduced Proteins

The nucleotide sequences of the Sequence Listing or amino acid sequences deduced from them were used as query sequences against databases such as GenBank, SwissProt, BLOCKS, and Pima II. These databases which contain previously identified and annotated sequences were searched for regions of homology (similarity) using BLAST, which stands for Basic Local Alignment Search Tool (Altschul, S. F. (1993) J. Mol. Evol. 36: 290–300; Altschul, S. F et al (1990) J. Mol. Biol. 215: 403–10).

BLAST produces alignments of both nucleotide and amino acid sequences to determine sequence similarity. Because of the local nature of the alignments, BLAST is especially useful in determining exact matches or in identifying homologs which may be of prokaryotic (bacterial) or eukaryotic (animal, fungal or plant) origin. Other algorithms such as the one described in Smith, R. F. and T. F. Smith (1992 Protein Engineering 5: 35–51), incorporated herein by reference, can be used when dealing with primary sequence patterns and secondary structure gap penalties. As disclosed in this application, the minimum length of the sequences in the Sequence Listing is 49 nucleotides, and the upper limit of uncalled bases where N is recorded rather than A, C, G, or T is 12%.

The BLAST approach, as detailed in Karlin and Altschul (1993; Proc. Nat. Acad. Sci. 90: 5873–7) and incorporated herein by reference searches matches between a query sequence and a database sequence, to evaluate the statistical significance of any matches found, and to report only those matches which satisfy the user-selected threshold of significance. In this application, threshold was set at $10^{-25}$ for nucleotides and $10^{-10}$ for peptides.

Incyte nucleotide sequence were searched against the GenBank databases for primate (prID, rodent (rod), and mammalian sequences (mam), and deduced amino acid sequences from the same clones are searched against GenBank functional protein databases, mammalian (mamp), vertebrate (vrtp) and eukaryote (eukp), for homology. The relevant database for a particular match were reported as a GIxxx±p (where xxx is pri, rod, etc and if present, p=peptide) as shown in Table 1.

IV Northern Analysis

Northern analysis is a laboratory technique used to detect the presence of a transcript of a gene and involves the hybridization of a labeled nucleotide sequence to a membrane on which RCAS from a particular cell type or tissue have been bound (Sambrook et al., supra).

Analogous computer techniques using BLAST (Altschul, S. F. (1993) J. Mol. Evol. 36: 290–300; Altschul, S. F. et al. (1990) J. Mol. Evol. 215: 403–410) are used to search for identical or related molecules in nucleotide databases such as GenBank or the LIFESEQ™ database (Incyte Pharmaceuticals). This analysis is much faster than multiple, membranebased hybridizations. In addition, the sensitivity of the computer search can be modified to determine whether any particular match is categorized as exact or homologous.

The basis of the search is the product score which is defined as:

$$\% \text{ sequence identity} \times \% \text{ maximum BLAST score}/100$$

The product score takes into account both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

The results of northern analysis are reported as a list of libraries in which the transcript encoding HSPHH occurs. Abundance and percent abundance are also reported. Abundance directly reflects the number of times a particular transcript is represented in a cDNA library, and percent abundance is abundance divided by the total number of sequences examined in the cDNA library.

V Extension of HSPHH Encoding Polynucleotides

The nucleic acid sequence of the Incyte Clone 2525691 and the Incyte Clone 3172266 were used to design oligonucleotide primers for extending a partial nucleotide sequence to full length. One primer was synthesized to initiate extension in the antisense direction, and the other was synthesized to extend sequence in the sense direction. Primers were used to facilitate the extension of the known sequence "outward" generating amplicons containing new, unknown nucleotide sequence for the region of interest. The initial primers were designed from the cDNA using OLIGO 4.06 (National Biosciences), or another appropriate program, to be about 22 to about 30 nucleotides in length, to have a GC content of 50% or more, and to anneal to the target sequence at temperatures of about 68° to about 72° C. Any stretch of nucleotides which would result in hairpin structures and primer-primer dimerizations was avoided.

Selected human CDNA libraries (Gibco/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. Beginning with 40 pmol of each primer and the recommended concentrations of all other components of the kit, PCR was performed using the Peltier Thermal Cycler (PTC200; M. J. Research, Watertown, Mass.) and the following parameters:

| Step 1  | 94° C. for 1 min (initial denaturation) |
|---------|------------------------------------------|
| Step 2  | 65° C. for 1 min                         |
| Step 3  | 68° C. for 6 min                         |
| Step 4  | 94° C. for 15 sec                        |
| Step 5  | 65° C. for 1 min                         |
| Step 6  | 68° C. for 7 min                         |
| Step 7  | Repeat step 4–6 for 15 additional cycles |
| Step 8  | 94° C. for 15 sec                        |
| Step 9  | 65° C. for 1 min                         |
| Step 10 | 68° C. for 7:15 min                      |
| Step 11 | Repeat step 8–10 for 12 cycles           |
| Step 12 | 72° C. for 8 min                         |
| Step 13 | 4° C. (and holding)                      |

A 5–10 µl aliquot of the reaction mixture was analyzed by electrophoresis on a low concentration (about 0.6–0.8%) agarose mini-gel to determine which reactions were successful in extending the sequence. Bands thought to contain the largest products were excised from the gel, purified using QIAQuick™ (QIAGEN Inc., Chatsworth, Calif.), and trimmed of overhangs using Klenow enzyme to facilitate religation and cloning.

After ethanol precipitation, the products were redissolved in 13 µl of ligation buffer, 1 µl T4-DNA ligase (15 units) and 1 µl T4 polynucleotide kinase were added, and the mixture was incubated at room temperature for 2–3 hours or overnight at 16° C. Competent E. coli cells (in 40 ∥1 of appropriate media) were transformed with 3 µl of ligation mixture and cultured in 80 µl of SOC medium (Sambrook et al., supra) After incubation for one hour at 37° C., the E. coli mixture was plated on Luria Bertani (LB)-agar (Sambrook et al., supra) containing 2x Carb. The following day, several colonies were randomly picked from each plate and cultured in 150 µl of liquid LB/2x Carb medium placed in an individual well of an appropriate, commercially-available, sterile 96-well microtiter plate. The following day, 5 µl of each overnight culture was transferred into a non-sterile 96-well plate and after dilution 1:10 with water, 5 µl of each sample was transferred into a PCR array.

For PCR amplification, 18 µl of concentrated PCR reaction mix (3.3x) containing 4 units of rTth DNA polymerase, a vector primer, and one or both of the gene specific primers used for the extension reaction were added to each well. Amplification was performed using the following conditions:

| Step 1 | 94° C. for 60 sec                         |
|--------|-------------------------------------------|
| Step 2 | 94° C. for 20 sec                         |
| Step 3 | 55° C. for 30 sec                         |
| Step 4 | 72° C. for 90 sec                         |
| Step 5 | Repeat steps 2–4 for an additional 29 cycles |
| Step 6 | 72° C. for 180 sec                        |
| Step 7 | 4° C. (and holding)                       |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequence of SEQ ID NO:2 and SEQ ID NO:4 is used to obtain 5' regulatory sequences using the procedure above, oligonucleotides designed for 5' extension, and an appropriate genomic library.

VI Labeling and Use of Individual Hybridization Probes

Hybridization probes derived from SEQ ID NO:2 and SEQ ID NO:4 are employed to screen cDNAs, genomic DNAs, or mRNAs. Although the labeling of oligonucleotides, consisting of about 20 base-pairs, is specifically described, essentially the same procedure is used with larger nucleotide fragments. Oligonucleotides are designed using state-of-the-art software such as OLIGO 4.06 (National Biosciences), labeled by combining 50 pmol of each oligomer and 250 µCi of [γ-$^{32}$P] adenosine triphosphate (Amersham) and T4 polynucleotide kinase (DuPont NEN®, Boston, Mass.). The labeled oligonucleotides are substantially purified with Sephadex G-25 superfine resin column (Pharmacia & Upjohn). A aliquot containing $10^7$ counts per minute of the labeled probe is used in a typical membrane-based hybridization analysis of human genomic DNA digested with one of the following endonucleases (Ase I, Bgl II, Eco RI, Pst I, Xba 1, or Pvu II; DuPont NEN®).

The DNA from each digest is fractionated on a 0.7 percent agarose gel and transferred to nylon membranes (Nytran Plus, Schleicher & Schuell, Durham, N.H.). Hybridization is carried out for 16 hours at 40° C. To remove nonspecific signals, blots are sequentially washed at room temperature under increasingly stringent conditions up to 0.1xsaline sodium citrate and 0.5% sodium dodecyl sulfate. After XOMAT AR™ film (Kodak, Rochester, N.Y.) is exposed to the blots in a Phosphoimager cassette (Molecular Dynamics, Sunnyvale, Calif.) for several hours, hybridization patterns are compared visually.

VII Microarrays

To produce oligonucleotides for a microarray, the nucleotide sequence described herein is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies 20 sequence-specific oligonucleotides of 20 nucleotides in length (20-mers). A matched set of oligonucleotides is created in which one nucleotide in the center of each sequence is altered. This process is repeated for each gene in the microarray, and double sets of twenty 20 mers are synthesized and arranged on the surface of the silicon chip using a light-directed chemical process (Chee, M. et al., PCT/WO95/11995, incorporated herein by reference).

In the alternative, a chemical coupling procedure and an ink jet device are used to synthesize oligomers on the surface of a substrate (Baldeschweiler, J.D. et al., PCT/WO95/25116, incorporated herein by reference). In another alternative, a "gridded" array analogous to a dot (or slot) blot is used to arrange and link cDNA fragments or oligonucleotides to the surface of a substrate using a vacuum system, thermal, UV, mechanical or chemical bonding procedures. An array may be produced by hand or using available materials and machines and contain grids of 8 dots, 24 dots, 96 dots, 384 dots, 1536 dots or 6144 dots. After hybridization, the microarray is washed to remove nonhybridized probes, and a scanner is used to determine the levels and patterns of fluorescence. The scanned images are examined to determine degree of complementarity and the relative abundance of each oligonucleotide sequence on the micro-array.

VIII Complementary Polynucleotides

Sequence complementary to the HSPHH-encoding sequence, or any part thereof, is used to decrease or inhibit expression of naturally occurring HSPHH. Although use of oligonucleotides comprising from about 15 to about 30 base-pairs is described, essentially the same procedure is used with smaller or larger sequence fragments. Appropriate oligonucleotides are designed using Oligo 4.06 software and the coding sequence of HSPHH, SEQ ID NO:1. To inhibit transcription, a complementary oligonucleotide is designed from the most unique 5' sequence and used to prevent promoter binding to the coding sequence. To inhibit translation, a complementary oligonucleotide is designed to prevent ribosomal binding to the HSPHH-encoding transcript.

IX Expression of HSPHH

Expression of HSPHH is accomplished by subcloning the cDNAs into appropriate vectors and transforming the vectors into host cells. In this case, the cloning vector is also used to express HSPHH in E. coli. Upstream of the cloning site, this vector contains a promoter for β-galactosidase, followed by sequence containing the amino-terminal Met, and the subsequent seven residues of β-galactosidase. Immediately following these eight residues is a bacteriophage promoter useful for transcription and a linker containing a number of unique restriction sites.

Induction of an isolated, transformed bacterial strain with IPTG using standard methods produces a fusion protein which consists of the first eight residues of β-galactosidase, about 5 to 15 residues of linker, and the full length protein. The signal residues direct the secretion of HSPHH into the bacterial growth media which can be used directly in the following assay for activity.

X Demonstration of HSPHH Activity

HSPHH induction by heat or toxins may be a demonstrated using primary cultures of human fibroblasts or human cell lines such as CCL-13, HEK293, or HEP G2 (ATCC). To heat induce HSPHH expression, aliquots of cells are incubated at 42° C. for 15, 30, or 60 minutes; control aliquots are incubated at 37° C. for the same time periods. To induce HSPHH expression by toxins, aliquots of cells are treated with 100 μM arsenite or 20 mM azetidine-2-carboxylic acid for 0, 3, 6, or 12 hours. After exposure to heat, arsinate, or the amino acid analogue, samples of the treated cells are harvested and cell lysates prepared for analysis by Western blot.

Cells are lysed in buffer containing 1% Nonidet P-40, 0.15 M NaCl, 50 mM Tris-HCl, 5 mM EDTA, 2 mMN-ethylmaleimide, 2 mM phenylmethylsulfonyl fluoride, 1 mg/ml leupeptin, and 1 mg/ml pepstatin. Twenty micrograms of the cell lysate is separated on an 8% SDS-PAGE gel and transferred to a nitrocellulose membrane. After blocking with 5% nonfat dry milk/phosphate-buffered saline for 1 h, the rembrane is incubated overnight at 4° C. or at room temperature for 2 to 4 hours with a 1:1000 dilution of anti-HSPHH serum in 2% nonfat dry milk/phosphate-buffered saline. The membrane is then washed and incubated with a 1:1000 dilution of horseradish peroxidase-conjugated goat anti-rabbit IgG (Cappel) in 2% dry milk/phosphate-buffered saline. After washing with 0.1% Tween 20 in phosphate-buffered saline, the HSPHH protein is detected and compared to controls by using the ECL system (Amersham).

XI Production of HSPHH Specific Antibodies

HSPHH that is substantially purified using PAGE electrophoresis (Sambrook, supra), or other purification techniques, is used to immunize rabbits and to produce antibodies using standard protocols. The amino acid sequence deduced from SEQ ID NO:2 is analyzed using DNASTAR software (DNASTAR Inc) to determine regions of high immunogenicity and a corresponding oligopeptide is synthesized and used to raise antibodies by means known to those of skill in the art. Selection of appropriate epitopes, such as those near the C-terminus or in hydrophilic regions, is described by Ausubel et al. (supra), and others.

Typically, the oligopeptides are 15 residues in length, synthesized using an Applied Biosystems Peptide Synthesizer Model 431A using fmoc-chemistry, and coupled to keyhole limpet hemocyanin (KLH, Sigma, St. Louis, Mo.) by reaction with N-maleimidobenzoyl-N-hydroxysuccinimide ester (MBS; Ausubel et al., supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radio iodinated, goat antirabbit IgG.

XII Purification of Naturally Occurring HSPHH Using Specific Antibodies

Naturally occurring or recombinant HSPHH is substantially purified by immunoaffinity chromatography using antibodies specific for HSPHH. An immunoaffinity column is constructed by covalently coupling HSPHH antibody to an activated chromatographic resin, such as CNBr-activated Sepharose (Pharmacia & Upjohn). After the coupling, the resin is blocked and washed according to the manufacturer's instructions.

Media containing HSPHH is passed over the immunoaffinity column, and the column is washed under conditions that allow the preferential absorbance of HSPHH (e.g., high ionic strength buffers in the presence of detergent). The column is eluted under conditions that disrupt antibody/HSPHH binding (eg, a buffer of pH 2–3 or a high concentration of a chaotrope, such as urea or thiocyanate ion), and HSPHH is collected.

XIII Identification of Molecules Which Interact with HSPHH

HSPHH or biologically active fragments thereof are labeled with $^{125}$I Bolton-Hunter reagent (Bolton et al. (1973) Biochem. J. 133: 529). Candidate molecules previously arrayed in the wells of a multi-well plate are incubated with the labeled HSPHH, washed and any wells with labeled HSPHH complex are assayed. Data obtained using different concentrations of HSPHH are used to calculate values for the number, affinity, and association of HSPHH with the candidate molecules.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
    (A) LENGTH: 348 amino acids
    (B) TYPE: amino acid
    (C) STRANDEDNESS: single
    (D) TOPOLOGY: linear (vii) IMMEDIATE SOURCE:
    (A) LIBRARY: BRAITUT21
    (B) CLONE: 2525691

(xi) SEQUENCE DESCRIPTION: SEQ ID NO:1:

```
Met Gly Lys Asp Tyr Tyr Lys Ile Leu Gly Ile Pro Ser Gly Ala Asn
1               5                   10                  15

Glu Asp Glu Ile Lys Lys Ala Tyr Arg Lys Met Ala Leu Lys Tyr His
            20                  25                  30

Pro Asp Lys Asn Lys Glu Pro Asn Ala Glu Glu Lys Phe Lys Glu Ile
            35                  40                  45

Ala Glu Ala Tyr Asp Val Leu Ser Asp Pro Lys Lys Arg Gly Leu Tyr
    50                  55                  60

Asp Gln Tyr Gly Glu Glu Gly Leu Lys Thr Gly Gly Gly Thr Ser Gly
65                  70                  75                  80

Gly Ser Ser Gly Ser Phe His Tyr Thr Phe His Gly Asp Pro His Ala
                85                  90                  95

Thr Phe Ala Ser Phe Phe Gly Gly Ser Asn Pro Phe Asp Ile Phe Phe
                100                 105                 110

Ala Ser Ser Arg Ser Thr Arg Pro Phe Ser Gly Phe Asp Pro Asp Asp
                115                 120                 125

Met Asp Val Asp Glu Asp Glu Asp Pro Phe Gly Ala Phe Gly Arg Phe
    130                 135                 140

Gly Phe Asn Gly Leu Ser Arg Gly Pro Arg Arg Ala Pro Glu Pro Leu
145                 150                 155                 160

Tyr Pro Arg Arg Lys Val Gln Asp Pro Pro Val Val His Glu Leu Arg
                165                 170                 175

Val Ser Leu Glu Glu Ile Tyr His Gly Ser Thr Lys Arg Met Lys Ile
                180                 185                 190

Thr Arg Arg Arg Leu Asn Pro Asp Gly Arg Thr Val Arg Thr Glu Asp
            195                 200                 205

Lys Ile Leu His Ile Val Ile Lys Arg Gly Trp Lys Glu Gly Thr Lys
    210                 215                 220

Ile Thr Phe Pro Lys Glu Gly Asp Ala Thr Pro Asp Asn Ile Pro Ala
```

```
225                 230                 235                 240
Asp Ile Val Phe Val Leu Lys Asp Lys Pro His Ala His Phe Arg Arg
                245                 250                 255

Asp Gly Thr Asn Val Leu Tyr Ser Ala Leu Ile Ser Leu Lys Glu Ala
                260                 265                 270

Leu Cys Gly Cys Thr Val Asn Ile Pro Thr Ile Asp Gly Arg Val Ile
            275                 280                 285

Pro Leu Pro Cys Asn Asp Val Ile Lys Pro Gly Thr Val Lys Arg Leu
        290                 295                 300

Arg Gly Glu Gly Leu Pro Phe Pro Lys Val Pro Thr Gln Arg Gly Asp
305                 310                 315                 320

Leu Ile Val Glu Phe Lys Val Arg Phe Pro Asp Arg Leu Thr Pro Gln
                325                 330                 335

Thr Arg Gln Ile Leu Lys Gln His Leu Pro Cys Ser
            340                 345
```

(2) INFORMATION FOR SEQ ID NO:2:

(i) SEQUENCE CHARACTERISTICS:
        (A) LENGTH: 2349 base pairs
        (B) TYPE: nucleic acid
        (C) STRANDEDNESS: single
        (D) TOPOLOGY: linear (vii) IMMEDIATE SOURCE:
        (A) LIBRARY: BRAITUT21
        (B) CLONE: 2525691

(xi) SEQUENCE DESCRIPTION: SEQ ID NO:2:

```
GGACGGAGCC GGGGGAGGGG GCAGCGGCTG TCTCACGGAC CACGGCGGCG CCCGCAGCTC    60

CTCACCGAAA CAAGGAGACC AGTGCTGGTC CAGTGGCTGT GATGGGAAAA GATTATTACA   120

AGATTCTTGG GATCCCATCG GGGGCCAACG AGGATGAGAT CAAGAAAGCC TACCGGAAGA   180

TGGCCTTGAA GTACCACCCA GACAAGAATA AGAACCCAA CGCTGAGGAG AAGTTTAAGG    240

AGATTGCAGA GGCCTATGAT GTGCTAAGTG ACCCCAAGAA CGGGGCCTG TATGACCAGT    300

ATGGGGAGGA AGGCCTGAAG ACCGGCGGTG GCACATCAGG TGGCTCCAGT GGCTCCTTTC   360

ACTACACCTT TCATGGGGAC CCCCATGCCA CCTTTGCCTC CTTCTTTGGT GGCTCCAACC   420

CCTTCGATAT CTTCTTTGCC AGCAGCCGCT CCACTCGGCC CTTCAGTGGC TTTGACCCAG   480

ATGACATGGA TGTGGATGAA GATGAGGACC CATTTGGCGC TTTCGGCCGT TTTGGCTTCA   540

ATGGGCTGAG TAGGGGTCCA AGGCGAGCCC CAGAACCACT GTACCCTCGG CGCAAGGTGC   600

AGGACCCCCC AGTGGTGCAC GAGCTGCGGG TGTCCCTGGA GGAGATCTAC CATGGCTCCA   660

CCAAGCGCAT GAAGATCACA AGGCGTCGCC TCAACCCTGA TGGGCGAACT GTGCGCACCG   720

AGGACAAGAT CCTGCACATA GTCATCAAGC GTGGCTGGAA GGAAGGCACC AAGATCACCT   780

TCCCCAAAGA AGGCGACGCC ACACCTGACA ACATCCCTGC TGACATCGTC TTTGTGCTCA   840

AAGACAAGCC CCATGCACAC TTCCGCCGAG ATGGCACCAA CGTGCTCTAC AGTGCCCTGA   900

TCAGCCTCAA GGAGGCGCTG TGTGGCTGCA CTGTGAACAT TCCCACTATC GACGGCCGAG   960

TGATCCCTTT GCCCTGCAAT GATGTCATCA AGCCAGGCAC CGTGAAGAGA CTCCGTGGGG  1020

AGGGCCTTCC CTTCCCCAAA GTGCCAACTC AGCGAGGAGA CCTCATTGTT GAGTTCAAAG  1080

TTCGCTTCCC AGACAGATTA ACACCACAGA CAAGACAGAT CCTTAAGCAG CACCTACCCT  1140

GTTCCTAGGC TCTGCCCCAG CCAGTCCAGA GCCTACCACA GCAATACCCC CAACACTCAC  1200

TCCACTCAAT GTGCACCCAG CTTGATGTCC ACTGGACACT GGCAACTTTT TCTAAAATGC  1260
```

-continued

```
AAAAAAAAGC CACTGGTTTT CAGGAAAATG TTCCTGTCCC TGACCCCTTT TAGAGCTGGG    1320

CTGCCTGGGG GGAGTTGGAG GGAGGTGGGG AGAGCTAGCC CAGGCCAGGG GTCAATGTTC    1380

ATGTCACTAG CTTTCAATCC AGTTTCCACT GCAGTGGCTG GAGAGTGACC TGAGTGCTAC    1440

TTGAAGATAT GTAGAGATTC CTTATCCATG CCTGTACATA GCATGTCCTC CTCCCCTCAG    1500

CTTTGCTAAT ACCAGTCCCC TCCCTTCCCT TTGGCTTCCT GCTGTTGGGG GTGGAAAAGA    1560

CTAGAAAGGA CATTGCTTTC TCAGCCCCAC CCCCAGGTCC ACAGTGTCCA AGGTAATGGC    1620

ACACATATTC ATGCACAAGA AGCACTCACC TAGAGCTGTC TGTGCCTCTC TGGGAGAAAG    1680

GAGAGAGGAT AAGAAGGGAA AGTTCACAAC CTGTGAACAG GGACTTGAGC ACGAGACACT    1740

TTTCATCTGG AGCAGGGGGG TGAGCTCCTC AGCAGCCTCC GTAACAGCTG CCCTGCCTAC    1800

ACCTGCAGAG CTGGAGGTTC TGTCCTCCCT GCTGCTCTCA GGAGTGTTCA AGGGTGGAGG    1860

GCAGGGAATG GGGCCTGAGG TATTAAGGCT AAGAGGTGGG GGACAGGGCC CATCTACCAG    1920

CCTTCATCAG GAAGGGAAAG GGCTTTGGGG TCAGGTGGCA GCTATTCCCC ACCAAGAGAT    1980

TCAGGGTCAC AGGTTTTTCC CCACACCTCT GAACTCAGGG CCTAGCCACC CCCAAACTTC    2040

CAAATCCCAC TTTTGTGATA TGTGAAGCTA CTCATTTCTT ACCCTTGGAG GCTGTGTGGG    2100

GAATTTCCAG CCCTTTTATG CCTGTGTGAT CCCACCCCAC CCCCATAGTT GTATAAAGGT    2160

CATAGTGAAG AAGCTGGGGG AAGACTGCTT CAGCCAGATC CTGGGGTGGG GTCTTTAGGT    2220

TTTCTCACTT TGACAACCCC CGAATGTTTT TATAGTAGTT TTTTTGTATT TTTTTGTAAT    2280

GACAGTATTA TGTAAAAAAT AAAGTATTTT AAAAATANAA AAAAATGTTC AAATCACAAG    2340

TGTCATGAT                                                           2349
```

(2) INFORMATION FOR SEQ ID NO:3:

(i) SEQUENCE CHARACTERISTICS:
        (A) LENGTH: 137 amino acids
        (B) TYPE: amino acid
        (C) STRANDEDNESS: single
        (D) TOPOLOGY: linear (vii) IMMEDIATE SOURCE:
        (A) LIBRARY: BRSTNOT18
        (B) CLONE: 3172266

(xi) SEQUENCE DESCRIPTION: SEQ ID NO:3:

```
Met Leu Gln Ala Pro Arg Gly Arg Ala Arg Ala Leu Arg Arg Leu
 1               5                  10                  15

Ala Val Ala Thr Arg Thr Met Ala Gly Ala Pro Thr Val Ser Leu Pro
                20                  25                  30

Glu Leu Arg Ser Leu Leu Ala Ser Gly Arg Ala Arg Leu Phe Asp Val
            35                  40                  45

Arg Ser Arg Glu Glu Ala Ala Ala Gly Thr Ile Pro Gly Ala Leu Asn
        50                  55                  60

Ile Pro Val Ser Glu Leu Glu Ser Ala Leu Gln Met Glu Pro Ala Ala
65                  70                  75                  80

Phe Gln Ala Leu Tyr Ser Ala Glu Lys Pro Lys Leu Glu Asp Glu His
                85                  90                  95

Leu Val Phe Phe Cys Gln Met Gly Lys Arg Gly Leu Gln Ala Thr Gln
                100                 105                 110

Leu Ala Arg Ser Leu Gly Tyr Thr Gly Ala Arg Asn Tyr Ala Gly Ala
            115                 120                 125

Tyr Arg Glu Trp Leu Glu Lys Glu Ser
        130                 135
```

(2) INFORMATION FOR SEQ ID NO:4:

(i) SEQUENCE CHARACTERISTICS:
        (A) LENGTH: 593 base pairs
        (B) TYPE: nucleic acid
        (C) STRANDEDNESS: single
        (D) TOPOLOGY: linear (vii) IMMEDIATE SOURCE:
        (A) LIBRARY: BRSTNOT18
        (B) CLONE: 3172266

(xi) SEQUENCE DESCRIPTION: SEQ ID NO:4:

```
TTCCGGATCC GGTCTCAGCT CTAGGAGGGA ACGGGAGATG TTGCAGGCGC CGAGAGGGCG    60

GGCCAGGGCC GCACTCCGGA GACTCGCGGT TGCTACGCGC ACCATGGCTG GAGCGCCCAC   120

GGTCTCGCTT CCTGAACTCC GTTCACTCCT AGCCTCCGGA CGGGCCCGGC TCTTCGACGT   180

GCGCTCTCGC GAGGAGGCGG CAGCTGGGAC CATCCCAGGG GCGCTCAACA TCCCGGTGTC   240

CGAGTTGGAG AGTGCTCTGC AGATGGAGCC AGCTGCCTTC CAGGCTTTAT ATTCTGCTGA   300

GAAGCCAAAG CTGGAAGATG AGCATCTCGT TTTCTTCTGT CAGATGGGCA AGCGGGGCCT   360

CCAGGCCACG CAGCTGGCCC GGAGTCTTGG ATACACTGGG GCTCGCAACT ACGCTGGAGC   420

CTATAGAGAA TGGTTGGAGA AAGAGAGTTA GGCAGGAGGC AGCTTACTGA TTGCCACCCC   480

CTGGCCCCTT AATGGCCACC TTAACTAAGG GTGTGAACGG GCTGACTTGG TGAATTGGGC   540

AACTCCTTAT AGTGTTGTGC ACACAAAAGC ATCAAATAAA GAACATTTAA TCA          593
```

(2) INFORMATION FOR SEQ ID NO:5:

(i) SEQUENCE CHARACTERISTICS:
        (A) LENGTH: 340 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1816452

(xi) SEQUENCE DESCRIPTION: SEQ ID NO:5:

```
Met Gly Lys Asp Tyr Tyr Gln Thr Leu Gly Leu Ala Arg Gly Ala Ser
1               5                   10                  15

Asp Glu Glu Ile Lys Arg Ala Tyr Arg Arg Gln Ala Leu Arg Tyr His
                20                  25                  30

Pro Asp Lys Asn Lys Glu Pro Gly Ala Glu Glu Lys Phe Lys Glu Ile
            35                  40                  45

Ala Glu Ala Tyr Asp Val Leu Ser Asp Pro Arg Lys Arg Glu Ile Phe
50                  55                  60

Asp Arg Tyr Gly Glu Glu Gly Leu Lys Gly Ser Gly Pro Ser Gly Gly
65                  70                  75                  80

Ser Gly Gly Gly Ala Asn Gly Thr Ser Phe Ser Tyr Thr Phe His Gly
                85                  90                  95

Asp Pro His Ala Met Phe Ala Glu Phe Phe Gly Gly Arg Asn Pro Phe
            100                 105                 110

Asp Thr Phe Phe Gly Gln Arg Asn Gly Glu Glu Gly Met Asp Ile Asp
        115                 120                 125

Asp Pro Phe Ser Gly Phe Pro Met Gly Met Gly Gly Phe Thr Asn Val
130                 135                 140

Asn Phe Gly Arg Ser Arg Ser Ala Gln Glu Pro Ala Arg Lys Lys Gln
145                 150                 155                 160
```

-continued

```
Asp Pro Pro Val Thr His Asp Leu Arg Val Ser Leu Glu Glu Ile Tyr
            165                 170                 175

Ser Gly Cys Thr Lys Lys Met Lys Ile Ser His Lys Arg Leu Asn Pro
            180                 185                 190

Asp Gly Lys Ser Ile Arg Asn Glu Asp Lys Ile Leu Thr Ile Glu Val
            195                 200                 205

Lys Lys Gly Trp Lys Glu Gly Thr Lys Ile Thr Phe Pro Lys Glu Gly
            210                 215                 220

Asp Gln Thr Ser Asn Asn Ile Pro Ala Asp Ile Val Phe Val Leu Lys
225                 230                 235                 240

Asp Lys Pro His Asn Ile Phe Lys Arg Asp Gly Ser Asp Val Ile Tyr
                245                 250                 255

Pro Ala Arg Ile Ser Leu Arg Glu Ala Leu Cys Gly Cys Thr Val Asn
                260                 265                 270

Val Pro Thr Leu Asp Gly Arg Thr Ile Pro Val Val Phe Lys Asp Val
            275                 280                 285

Ile Arg Pro Gly Met Arg Arg Lys Val Pro Gly Glu Gly Leu Pro Leu
            290                 295                 300

Pro Lys Thr Pro Glu Lys Arg Gly Asp Leu Ile Ile Glu Phe Glu Val
305                 310                 315                 320

Ile Phe Pro Glu Arg Ile Pro Gln Thr Ser Arg Thr Val Leu Glu Gln
                325                 330                 335

Val Leu Pro Ile
            340

(2) INFORMATION FOR SEQ ID NO:6:

(i) SEQUENCE CHARACTERISTICS:
        (A) LENGTH: 139 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 1279709

(xi) SEQUENCE DESCRIPTION: SEQ ID NO:6:

Met Trp Lys Ala Val Met Asn Ala Trp Asn Gly Thr Glu Ser Gln Ser
1               5                   10                  15

Lys Asn Val Ser Asn Ile Gln Ser Tyr Ser Phe Glu Asp Met Lys Arg
                20                  25                  30

Ile Val Gly Lys His Asp Pro Asn Val Leu Val Asp Val Arg Glu
            35                  40                  45

Pro Ser Glu Tyr Ser Ile Val His Ile Pro Ala Ser Ile Asn Val Pro
50                  55                  60

Tyr Arg Ser His Pro Asp Ala Phe Ala Leu Asp Pro Leu Glu Phe Glu
65                  70                  75                  80

Lys Gln Ile Gly Ile Pro Lys Pro Asp Ser Ala Lys Glu Leu Ile Phe
            85                  90                  95

Tyr Cys Ala Ser Gly Lys Arg Gly Gly Glu Ala Gln Lys Val Ala Ser
            100                 105                 110

Ser His Gly Tyr Ser Asn Thr Ser Leu Tyr Pro Gly Ser Met Asn Asp
            115                 120                 125

Trp Val Ser His Gly Gly Asp Lys Leu Asp Leu
            130                 135
```

What is claimed is:

1. An isolated and purified polynucleotide sequence encoding a polypeptide comprising the amino acid sequence of SEO ID NO:1.

2. A composition comprising the polynucleotide sequence of claim 1 and a carrier.

3. An isolated and purified polynucleotide sequence which is completely complementary to the polynucleotide sequence of claim 1.

4. An isolated and purified polynucleotide sequence comprising a polynucleotide sequence selected from the group consisting of SEQ ID NO:2 and SEQ ID NO:4.

5. An isolated and purified polynucleotide sequence which is completely complementary to the polynucleotide sequence of claim 4.

6. An expression vector containing the polynucleotide sequence of claim 1.

7. A host cell containing the expression vector of claim 6.

8. A method for producing a polypeptide comprising the amino acid sequence of SEQ ID NO:1 or SEQ ID NO:3, the method comprising the steps of:

a) culturing the host cell of claim 7 under conditions suitable for the expression of the polypeptide; and b) recovering the polypeptide from the host cell culture.

9. A method for detecting a polynucleotide encoding a polypeptide comprising the amino acid sequence of SEO ID NO:1 in a biological sample, the method comprising the steps of:

(a) hybridizing the polynucleotide of claim 3 to nucleic acids in the biological sample, thereby forming a hybridization complex;

(b) washing the hybridization complex under wash conditions of 0.1× saline sodium citrate and 0.5% sodium dodecyl sulfate at room temperature; and (c) detecting the hybridization complex, wherein the presence of the hybridization complex correlates with the presence of a polynucleotide encoding the polypeptide in the biological sample.

10. The method of claim 9 wherein the nucleic acids are amplified by the polymerase chain reaction prior to hybridization.

* * * * *